United States Patent
Lesnicki et al.

(10) Patent No.: US 11,597,758 B2
(45) Date of Patent: *Mar. 7, 2023

(54) FERMENTATION PROCESS FOR ANTIBODY PRODUCTION

(71) Applicant: H. LUNDBECK A/S, Valby (DK)

(72) Inventors: Gary Lesnicki, Woodinville, WA (US); Patricia Dianne McNeill, Federal Way, WA (US); Franz Hartner, Kundl (AT); Mark Young, Boulder, CO (US)

(73) Assignee: H. LUNDBECK A/S, Valby (DK)

( * ) Notice: Subject to any disclaimer, the term of this patent is extended or adjusted under 35 U.S.C. 154(b) by 388 days.

This patent is subject to a terminal disclaimer.

(21) Appl. No.: 16/258,014

(22) Filed: Jan. 25, 2019

(65) Prior Publication Data
US 2019/0211080 A1 Jul. 11, 2019

Related U.S. Application Data

(62) Division of application No. 14/776,865, filed as application No. PCT/US2014/030311 on Mar. 17, 2014, now Pat. No. 10,189,892.

(60) Provisional application No. 61/790,613, filed on Mar. 15, 2013.

(51) Int. Cl.
| C07K 16/00 | (2006.01) |
| C12P 21/02 | (2006.01) |
| C12P 21/00 | (2006.01) |
| C12N 15/63 | (2006.01) |
| C12N 15/67 | (2006.01) |
| C12N 15/81 | (2006.01) |

(52) U.S. Cl.
CPC .............. *C07K 16/00* (2013.01); *C12P 21/00* (2013.01); *C12P 21/02* (2013.01); *C07K 2317/14* (2013.01); *C12N 15/63* (2013.01); *C12N 15/67* (2013.01); *C12N 15/815* (2013.01)

(58) Field of Classification Search
None
See application file for complete search history.

(56) References Cited

U.S. PATENT DOCUMENTS

| 6,220,076 | B1 | 4/2001 | Layzell et al. |
| 7,892,825 | B2 | 2/2011 | Barr et al. |
| 2003/0228567 | A1 | 12/2003 | Famili et al. |
| 2010/0112369 | A1 | 5/2010 | Carlson et al. |
| 2011/0014650 | A1 | 1/2011 | Young et al. |

FOREIGN PATENT DOCUMENTS

| EP | 0 537 897 | 4/1996 |
| JP | 2006288201 | 10/2006 |
| WO | 2012049179 | 4/2012 |

OTHER PUBLICATIONS

Qian, et al. "Stimultaneous expression of antibody light and heavy chains in Pichia pastoris: improving retransfermation outcome by linearizing vector at a different site," Appl Microbiol Biotechnol. Dec. 2012;96(5):1381-90 (11 pages).

*Primary Examiner* — Marianne P Allen
(74) *Attorney, Agent, or Firm* — Robin L. Teskin; Baker, Donelson, Bearman, Caldwell & Berkowitz PC

(57) ABSTRACT

A feedback control mechanism for a fermentation of yeast cells to make recombinant proteins uses a respiratory quotient measurement which adjusts the levels of oxygenation and/or fermentable sugar feed. The feedback control mechanism permits well controlled cultures that produce good amounts of product while avoiding toxic accumulation of ethanol. Additionally, recombinant proteins so produced have excellent qualitative properties, such as excellent homogeneity and proper inter-subunit assembly.

10 Claims, 24 Drawing Sheets mAb1
3 Strains

A312 = mAb1 Strain A  Feed rate = 11 g/l/hr, 11 g/l Etoh bolus, RQ = 1.09 – 1.15
A326 = mAb1 Strain B  Feed rate = 11 g/l/hr, 11 g/l Etoh bolus, RQ = 1.09 – 1.15
A343 = mAb1 Strain C  Feed rate = 11 g/l/hr, 11 g/l Etoh bolus, RQ = 1.09 – 1.15

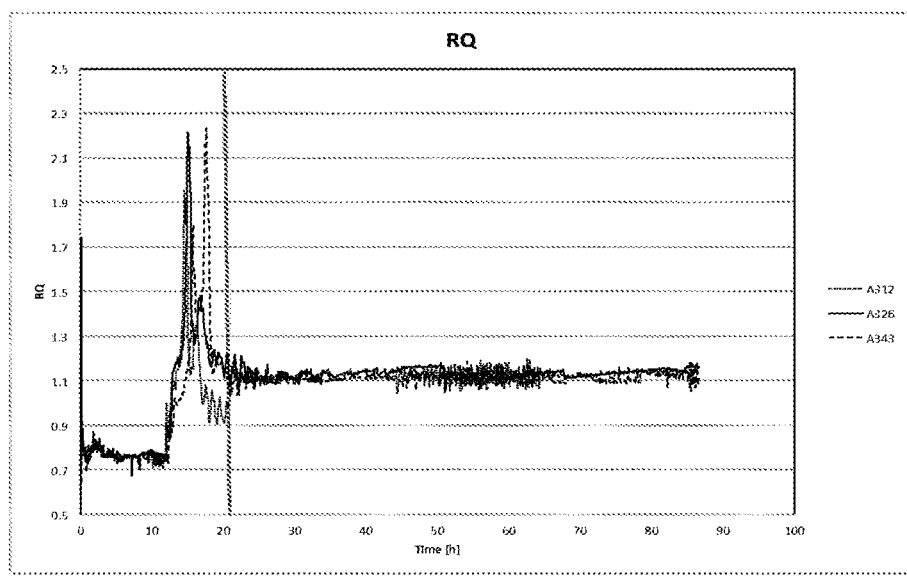

Figure 1: RQ control profile for 3 different mAb1 antibody strains A, B & C in 20L fermenters.

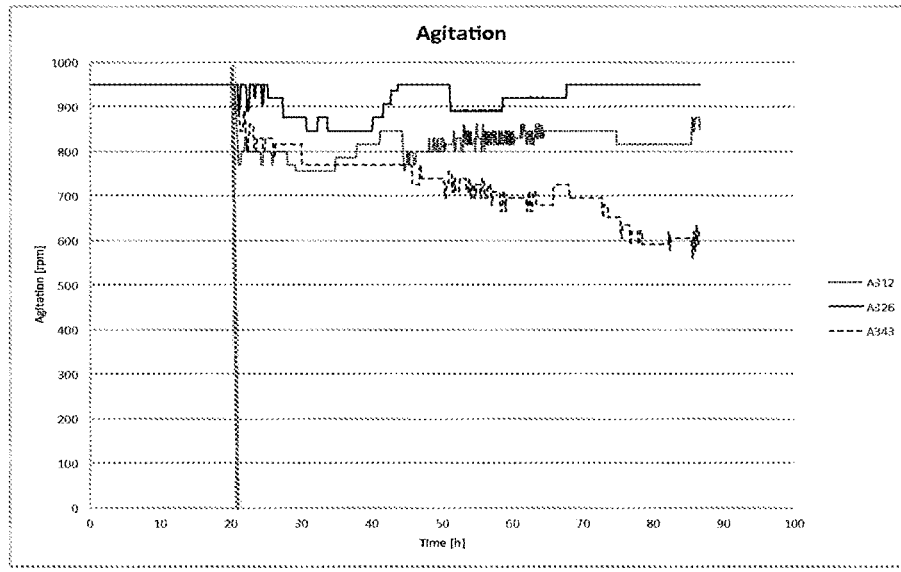

Figure 2: Agitation profile indicating agitation response to maintain desired RQ for 3 different mAb1 antibody strains A, B & C in 20L fermentors

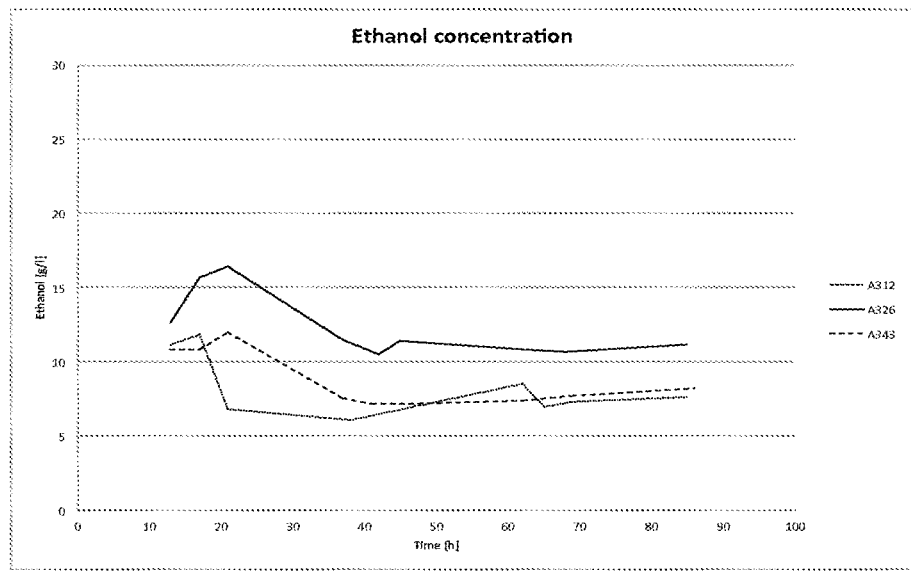
Figure 3: Ethanol concentration profile indicating effect of RQ control on maintaining non toxic ethanol levels for 3 different mAb1 antibody strains A, B & C in 20L fermentors
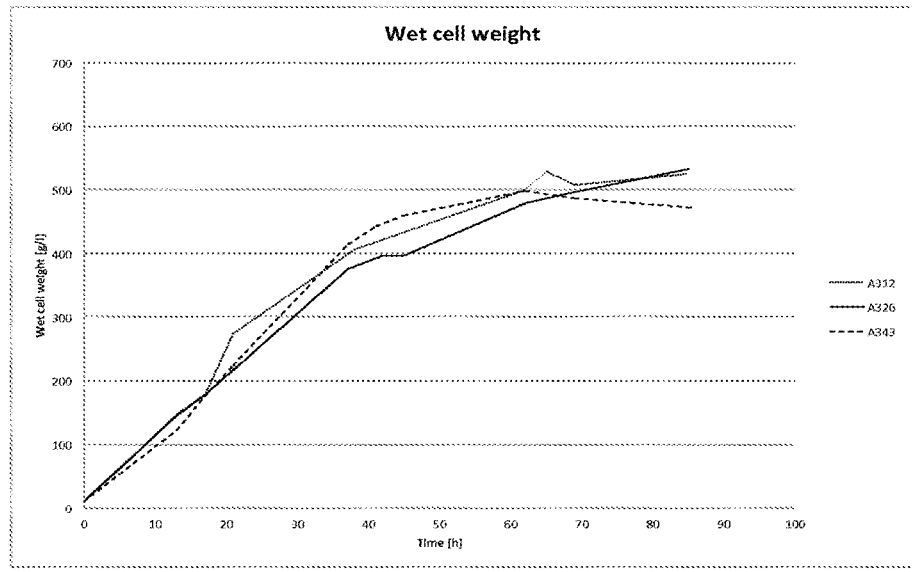
Figure 4: Cell growth profile indicating cellular growth similarity for 3 different mAb1 antibody strains A, B & C in 20L fermentors.

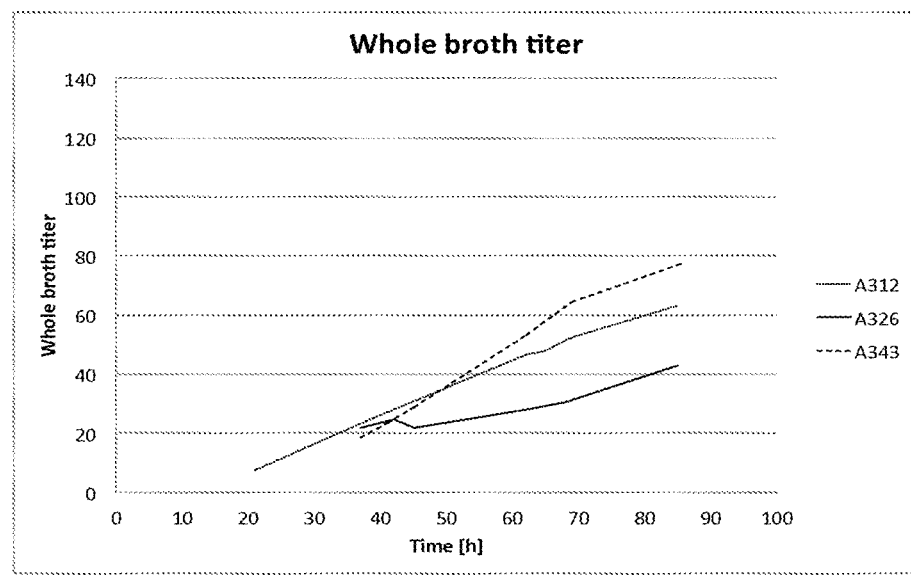
Figure 5: Whole Broth Titer profile indicating product expression for 3 different anti mAb1 antibody strains A, B & C in 20L fermentors

3 RQ Setpoints

A277 = mAb1 Strain A Feed rate = 11 g/l/hr, 11 g/l Etoh bolus, RQ = 1.19 – 1.25
A278 = mAb1 Strain A Feed rate = 11 g/l/hr, 11 g/l Etoh bolus, RQ = 1.29 – 1.35
A296 = mAb1 Strain A Feed rate = 11 g/l/hr, 11 g/l Etoh bolus, RQ = 1.09 – 1.15

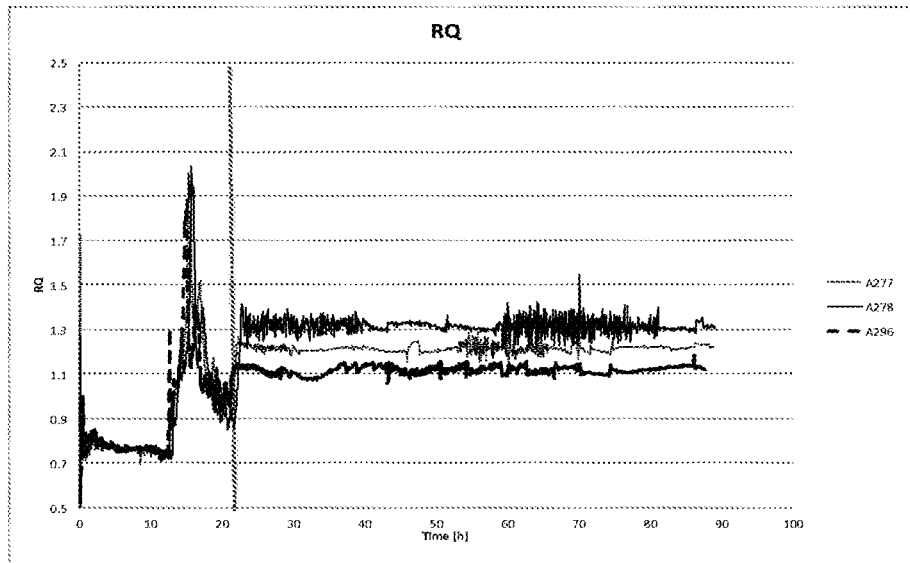

Figure 6: RQ control profile for 3 RQ control set points for mAb1 antibody Strain A in 20L fermentors

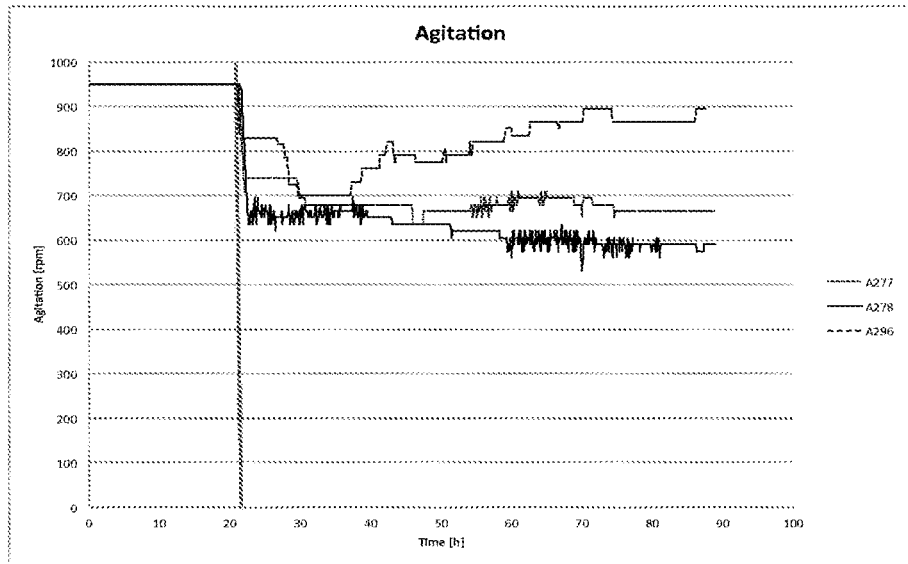

Figure 7: Agitation profile for 3 RQ control set points indicating agitation response to maintain desired RQ for mAb1 antibody Strain A 20L fermentors

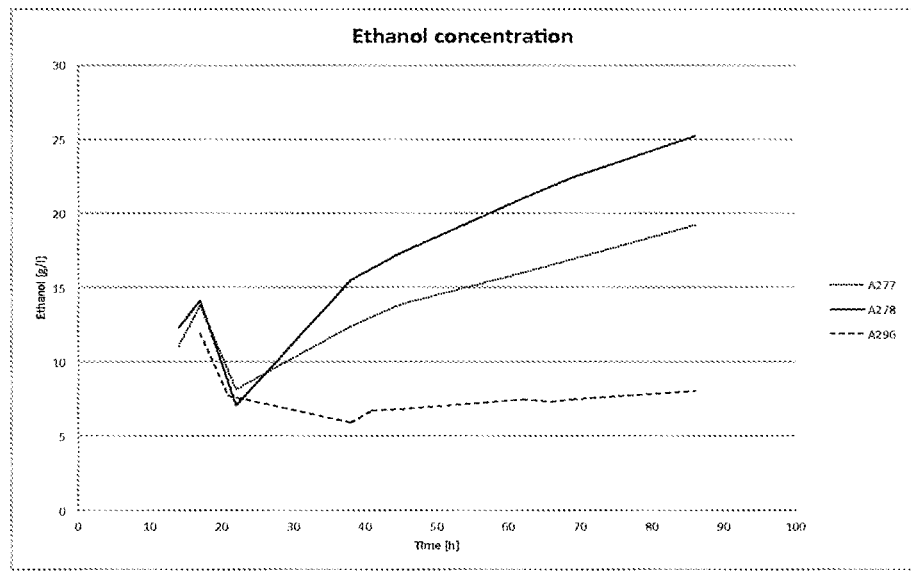
Figure 8: Ethanol concentration profile for 3 RQ control set points indicating effect of RQ control on maintaining non toxic ethanol levels for mAb1 antibody Strain A in 20L fermentors
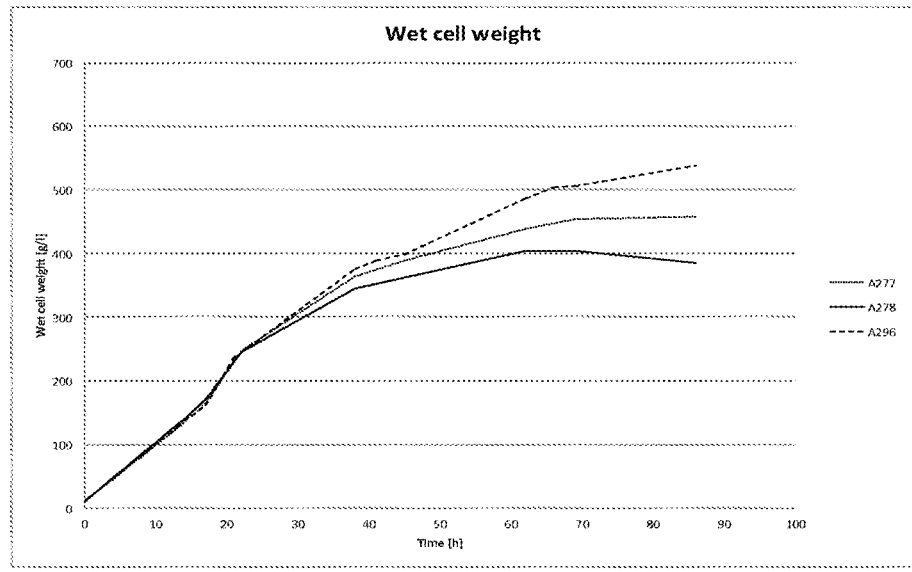
Figure 9: Cell growth profile for 3 RQ control set points indicating cellular growth for mAb1 antibody Strain A in 20L fermentors

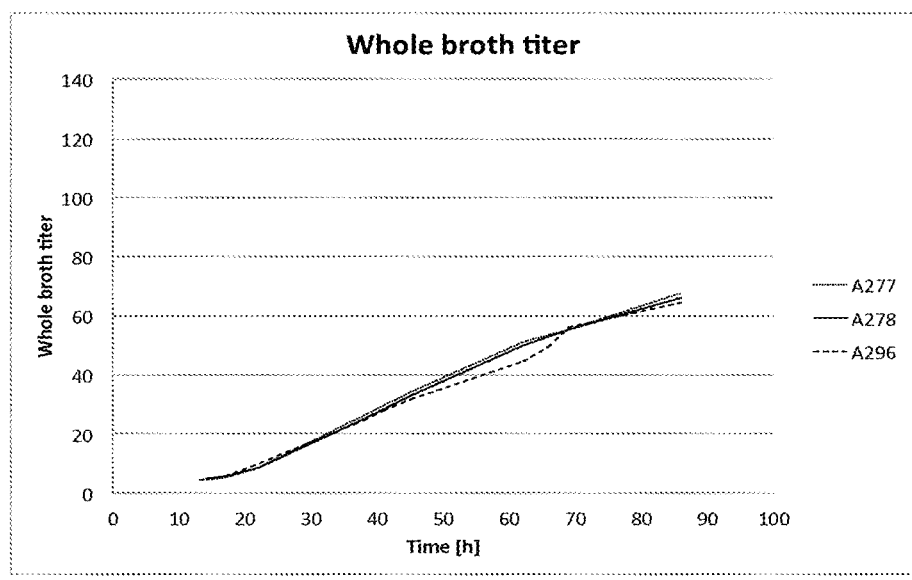
Figure 10: Whole Broth Titer profile for 3 RQ control set points indicating product expression for mAb1 antibody Strain A in 20L fermentors

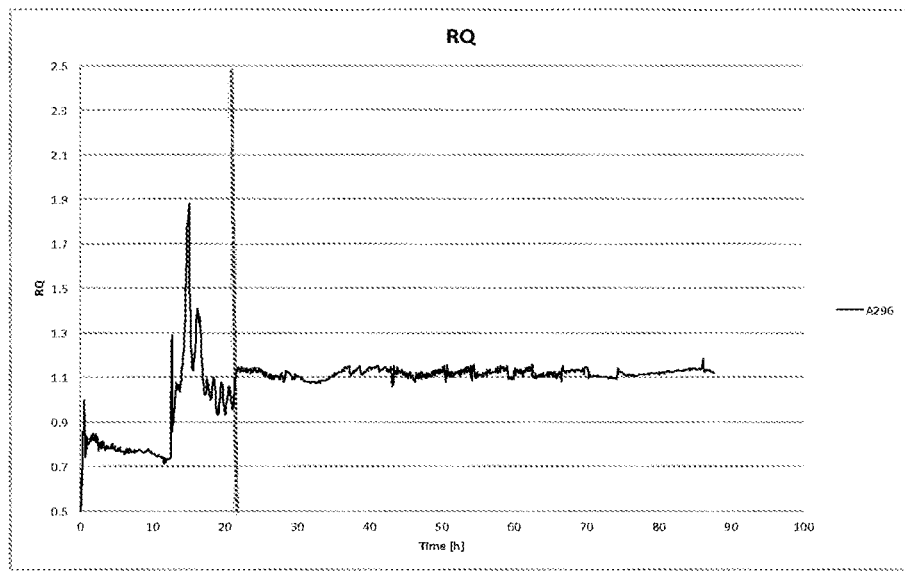

Figure 11: RQ control profile for comparison of aerobic and hypoxic state oxygenation for mAb1 antibody Strain A in 20L fermentors. Both fermentations were run at the same feed rates. RQ profile is not shown for the aerobic state.

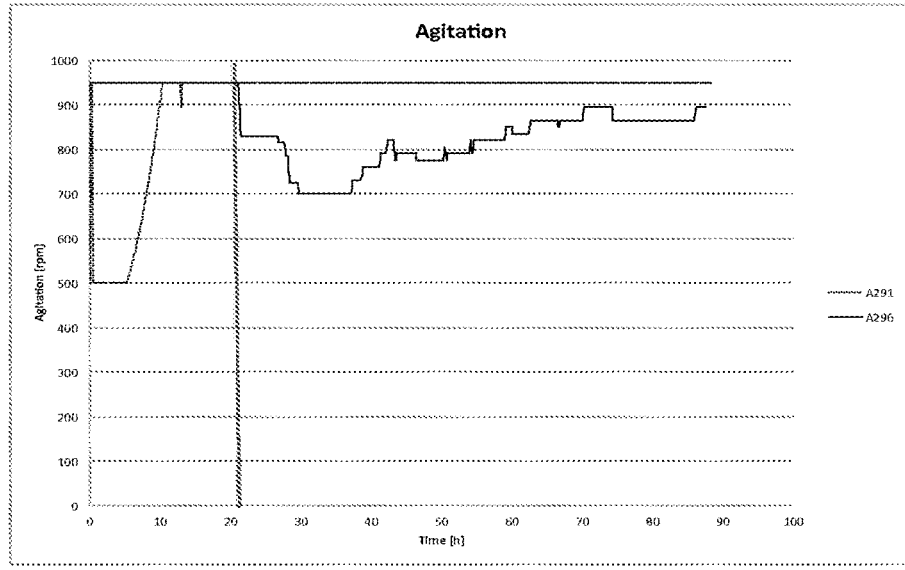

Figure 12: Agitation profile indicating agitation response to maintain desired RQ for hypoxic fermentation and constant agitation for aerobic fermentation for mAb1 antibody Strain A in 20L fermentors

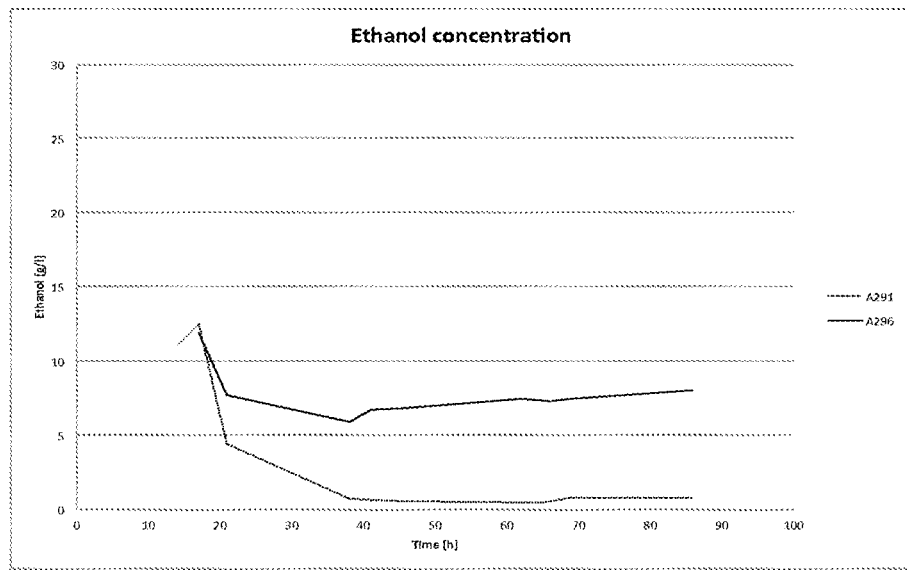

Figure 13: Ethanol concentration profile indicating effect of RQ control on maintaining non toxic ethanol levels for hypoxic fermentation and non fermentative state for aerobic fermentation for mAb1 antibody Strain A in 20L fermentors

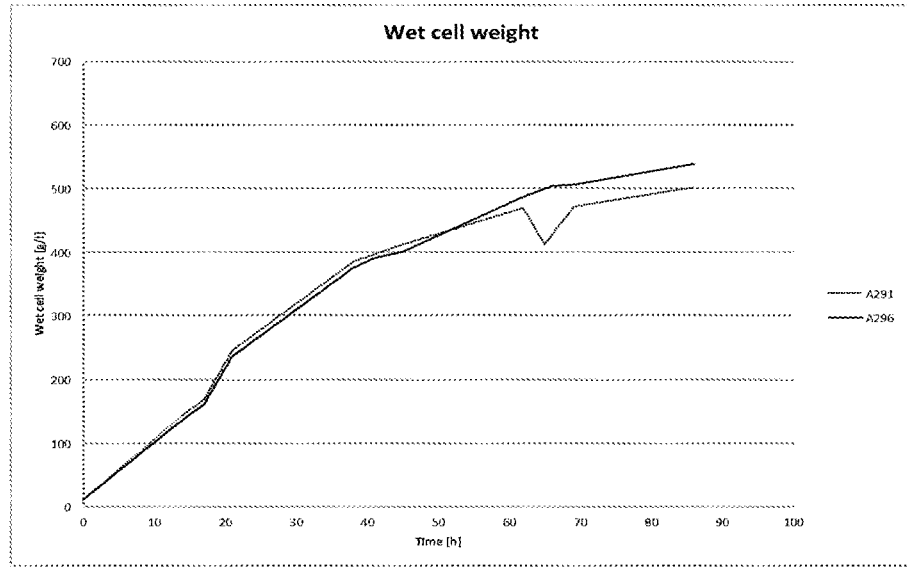

Figure 14: Cell growth profile indicating cellular growth similarity for hypoxic fermentation and aerobic fermentation for mAb1 antibody Strain A in 20L fermentors

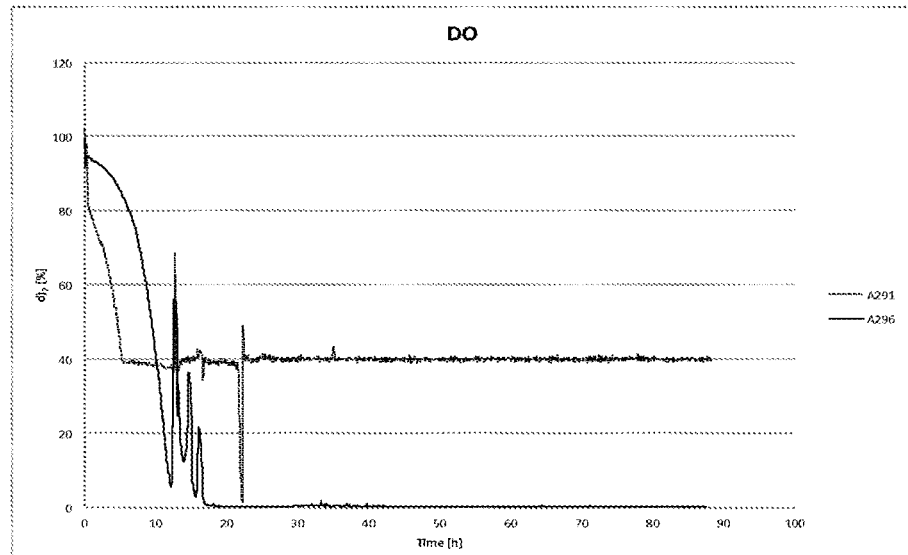

Figure 15: % DO (air saturation) profile indicating a controlled 40% DO (air saturation) for aerobic fermentation and a non measurable %DO (air saturation) after 17hrs for the hypoxic fermentation for mAb1 antibody Strain A in 20L fermentors

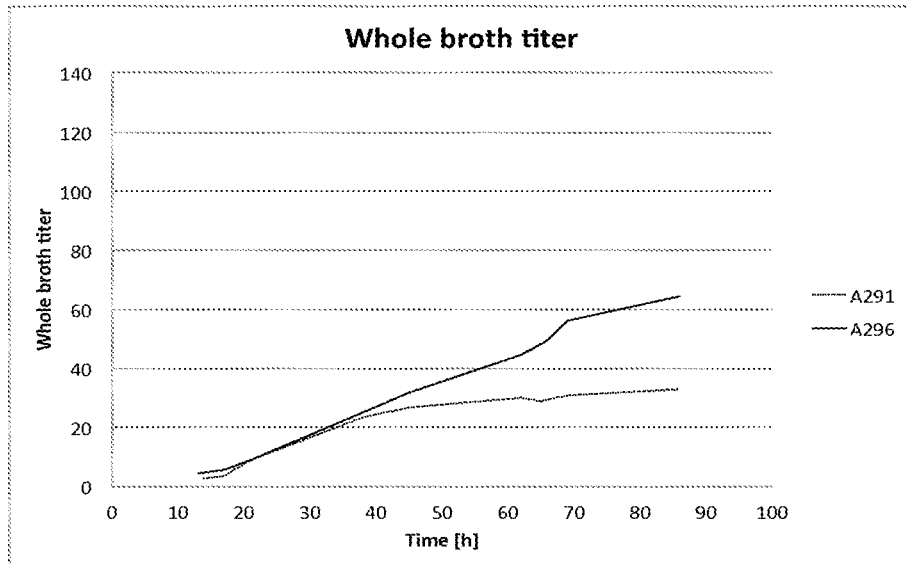

Figure 16: Whole Broth Titer profile indicating product expression for hypoxic and aerobic fermentations for mAb1 antibody Strain A in 20L fermentors mAb2

4 Strains

A158 = mAb2 Strain A  Feed rate = 18/15 step, RQ = 1.09-1.15, No Etoh bolus
A162 = mAb2 Strain B  Feed rate = 18/15 step, RQ = 1.09-1.15, No Etoh bolus
A163 = mAb2 Strain C  Feed rate = 18/15 step, RQ = 1.09-1.15, No Etoh bolus
A173 = mAb2 Strain D  Feed rate = 18/15 step, RQ = 1.09-1.15, No Etoh bolus

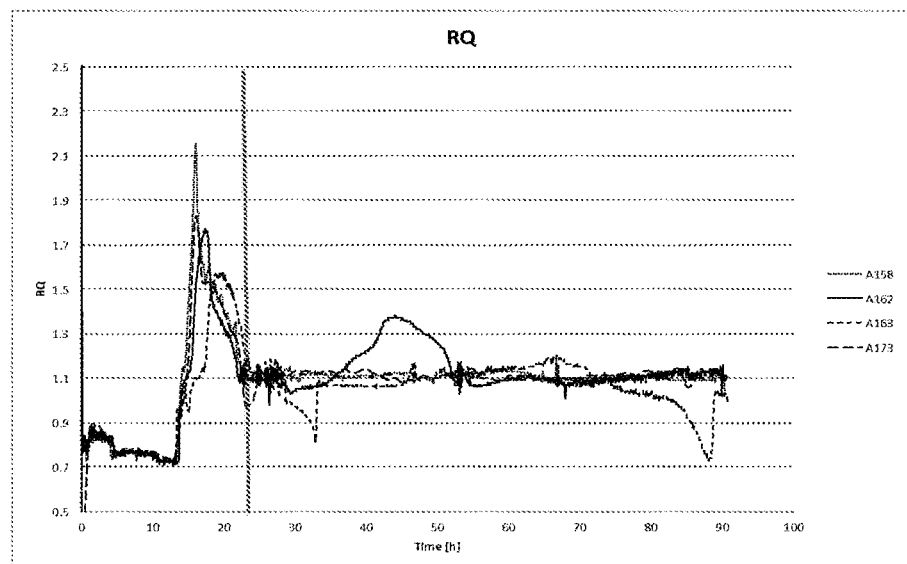

Figure 17: RQ control profile for 4 different mAb2 antibody Strains A, B, C & D in 20L fermentors

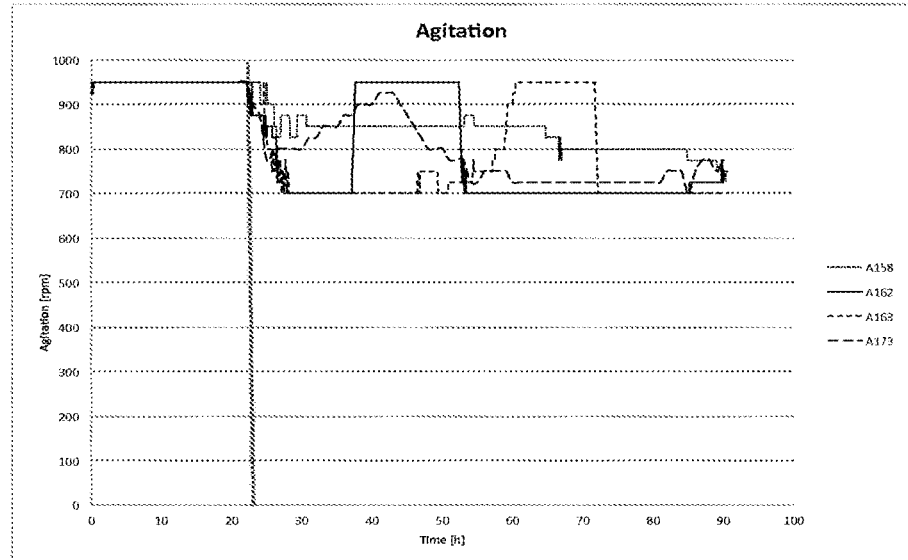

Figure 18: Agitation profile indicating agitation response to maintain desired RQ for 4 different mAb2 antibody Strains A, B, C & D in 20L fermentors

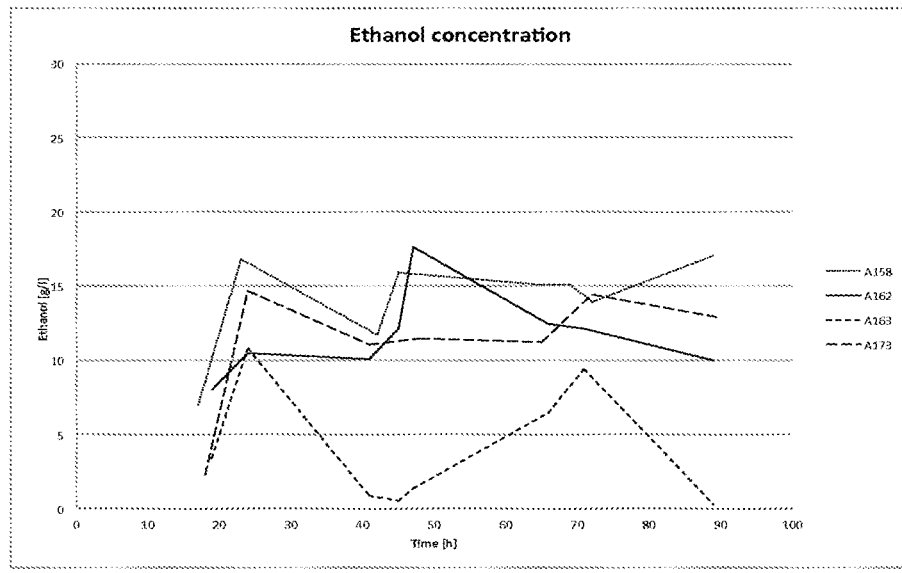
Figure 19: Ethanol concentration profile indicating effect of RQ control on maintaining non toxic ethanol levels for 4 different mAb2 antibody Strains A, B, C & D in 20L fermentors
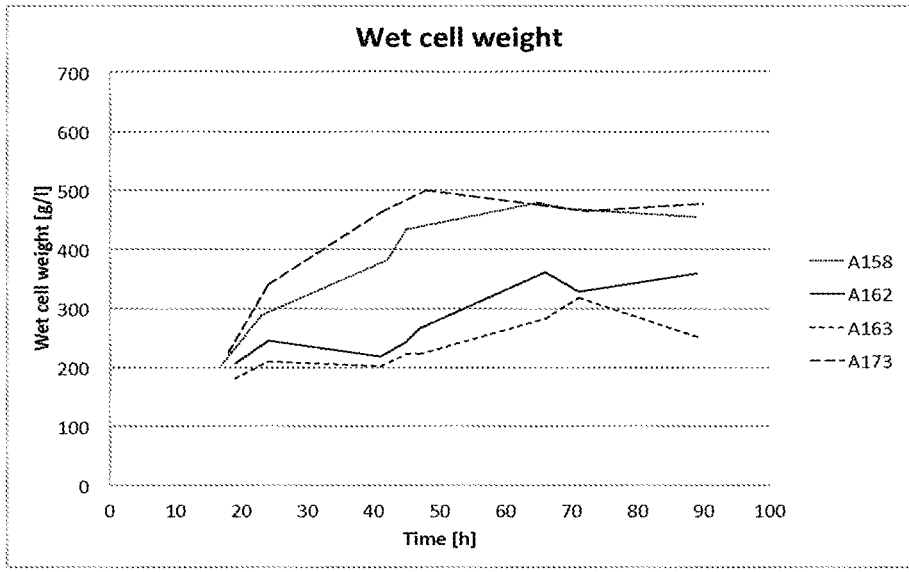
Figure 20: Cell growth profile indicating cellular growth differences for 4 different mAb2 antibody Strains A, B, C & D in 20L fermentors

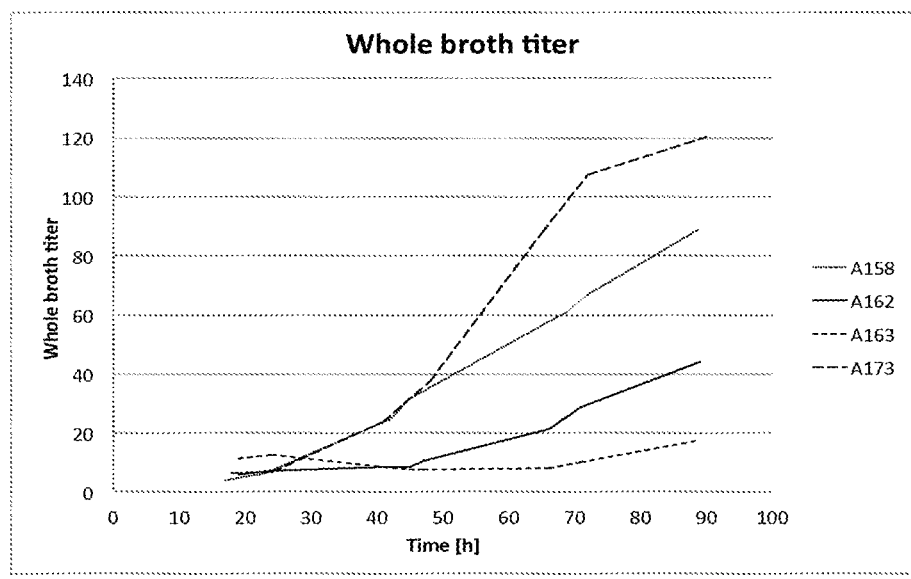
Figure 21: Whole Broth Titer profile indicating product expression for 4 different mAb2 antibody Strains A, B, C & D in 20L fermentors

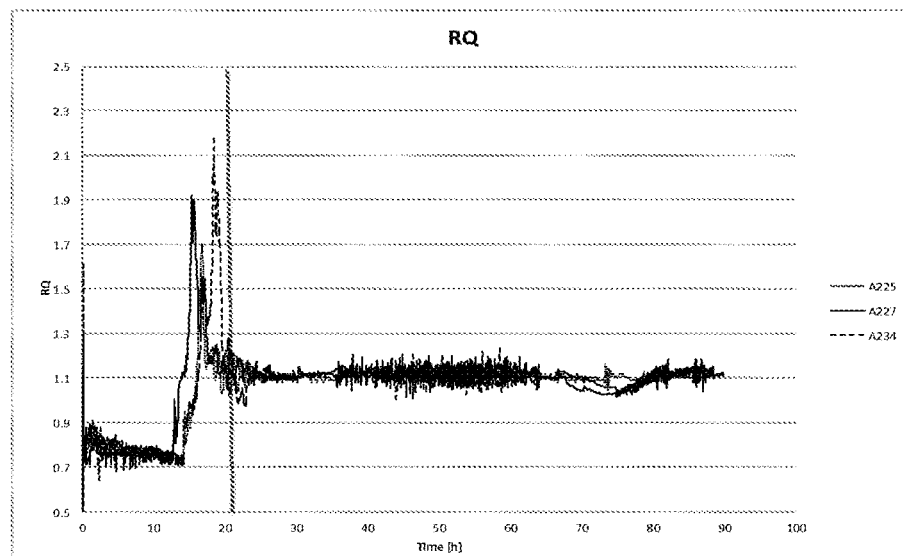
Figure 22: RQ control profile for 3 different mAb3 antibody Strains A, B & C in 20L fermentors
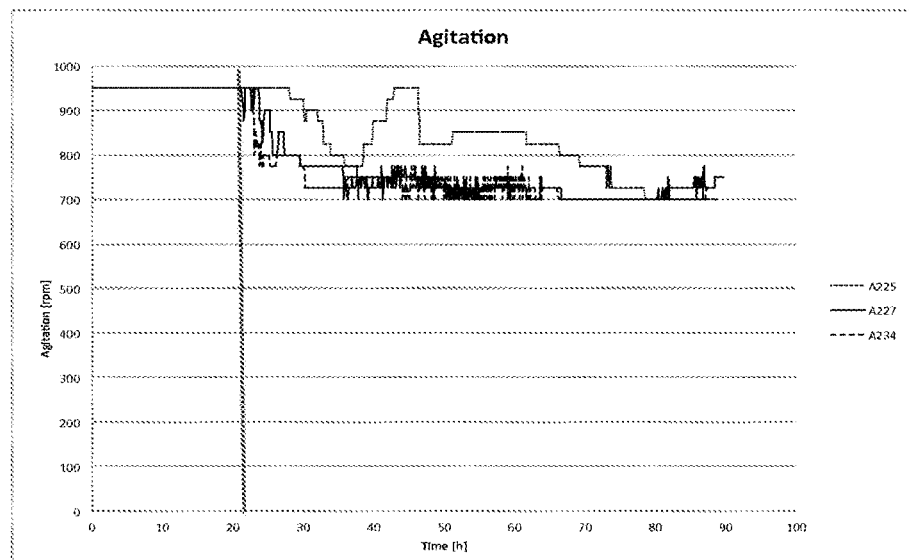
Figure 23: Agitation profile indicating agitation response to maintain desired RQ for 3 different mAb3 antibody Strains A, B & C in 20L fermentors

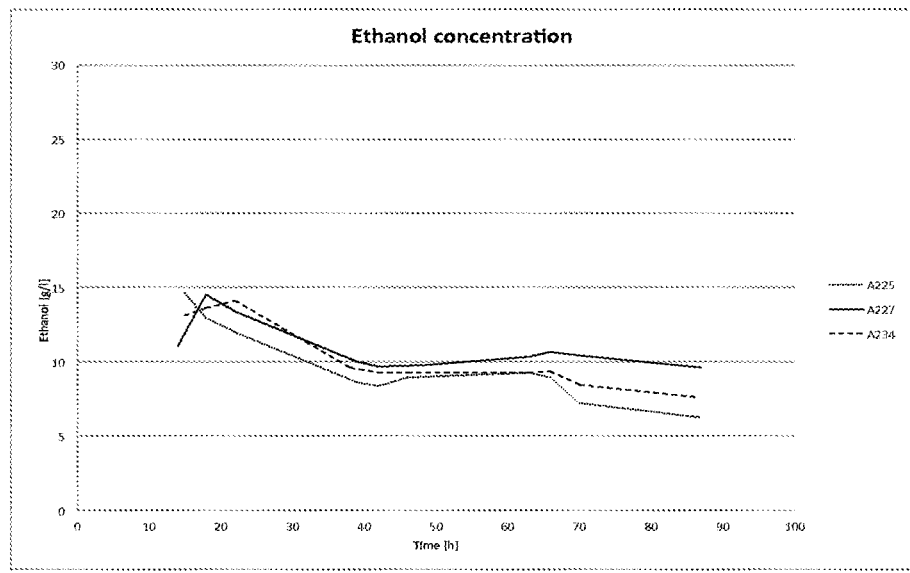
Figure 24: Ethanol concentration profile indicating effect of RQ for 3 different mAb3 antibody Strains A, B & C in 20L fermentors
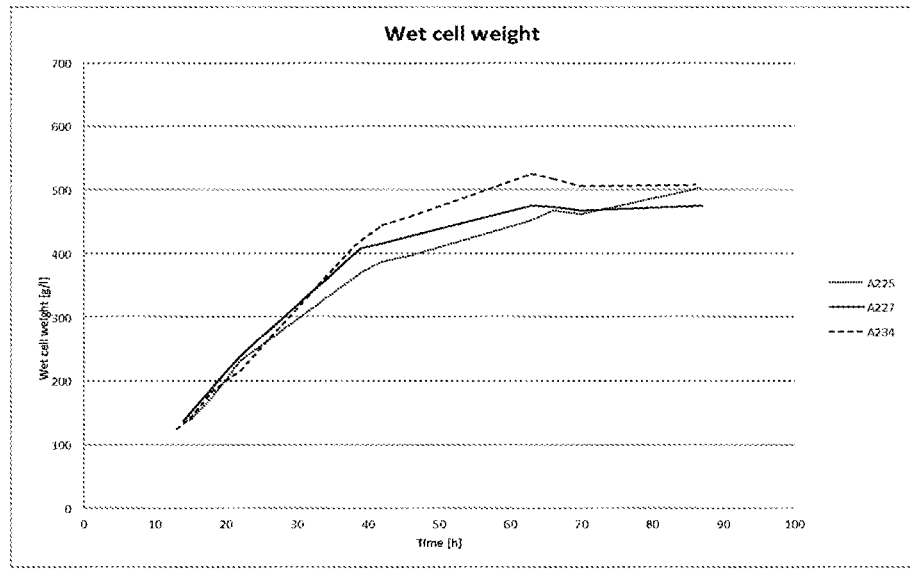
Figure 25: Cell growth profile indicating cellular growth for 3 different mAb3 antibody Strains A, B & C in 20L fermentors

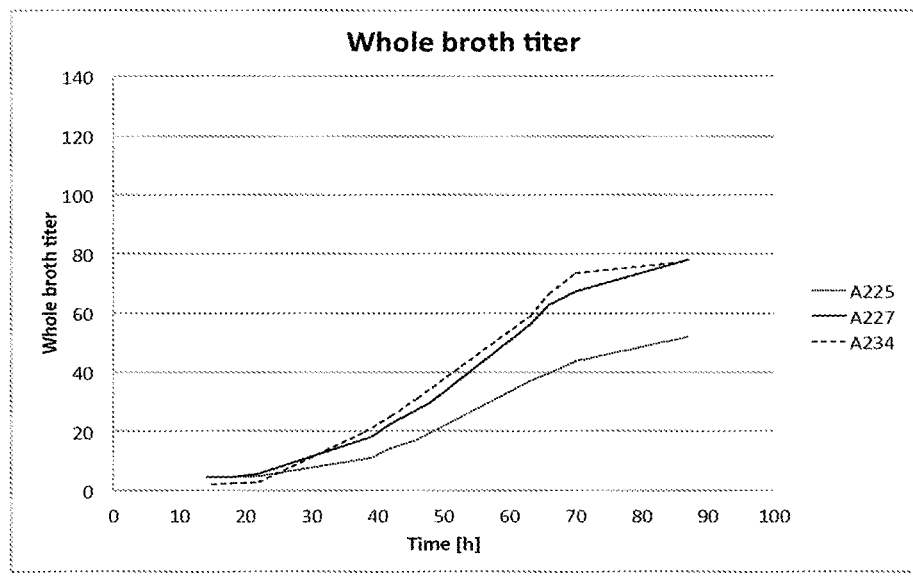
Figure 26: Whole Broth Titer profile indicating product expression for 3 different mAb3 antibody Strains A, B & C in 20L fermentors mAb3
4 Feed Rates

A226 = mAb3 Strain B Feed Rate = 9 g/l/hr, 11g/l Etoh bolus, RQ = 1.09 – 1.15
A230 = mAb3 Strain B Feed Rate = 11g/l/hr, 11g/l Etoh bolus, RQ = 1.09 – 1.15
A235 = mAb3 Strain B Feed Rate = 6 g/l/hr, 11g/l Etoh bolus, RQ = 1.09 – 1.15
A238 = mAb3 Strain B Feed Rate = 7 g/l/hr, 11g/l Etoh bolus, RQ = 1.09 – 1.15

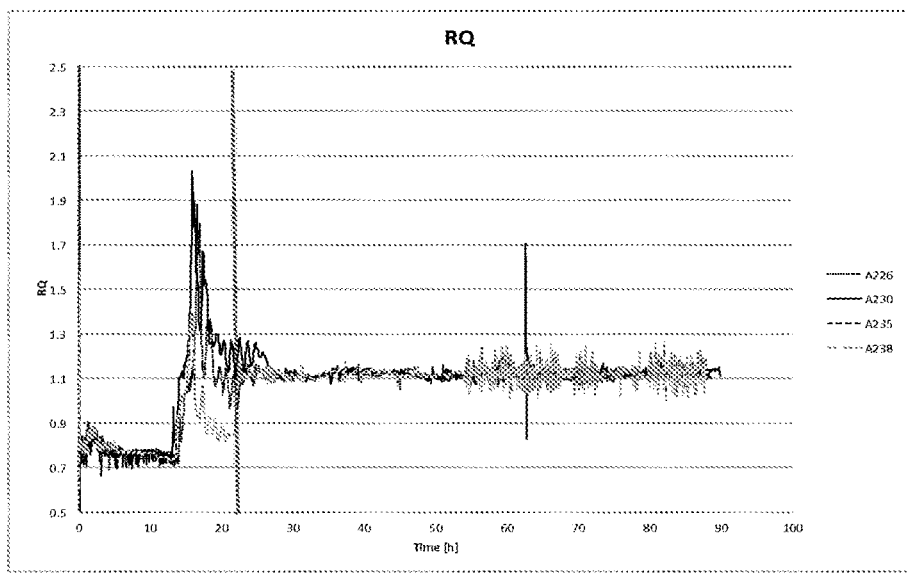

Figure 27: RQ control profile for 4 different feed rates for mAb3 antibody Strain B in 20L fermentors

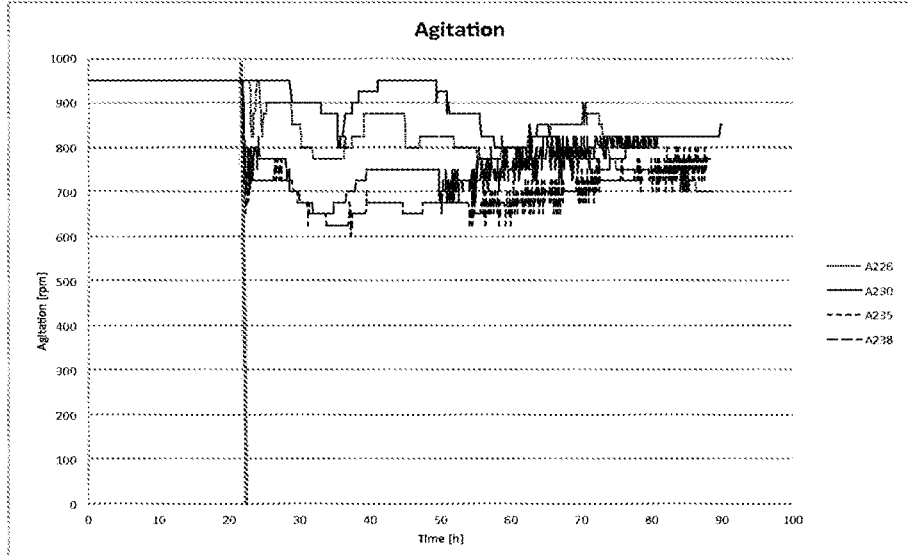

Figure 28: Agitation profile for 4 different feed rates indicating agitation response to maintain desired RQ for mAb3 antibody Strain B in 20L fermentors

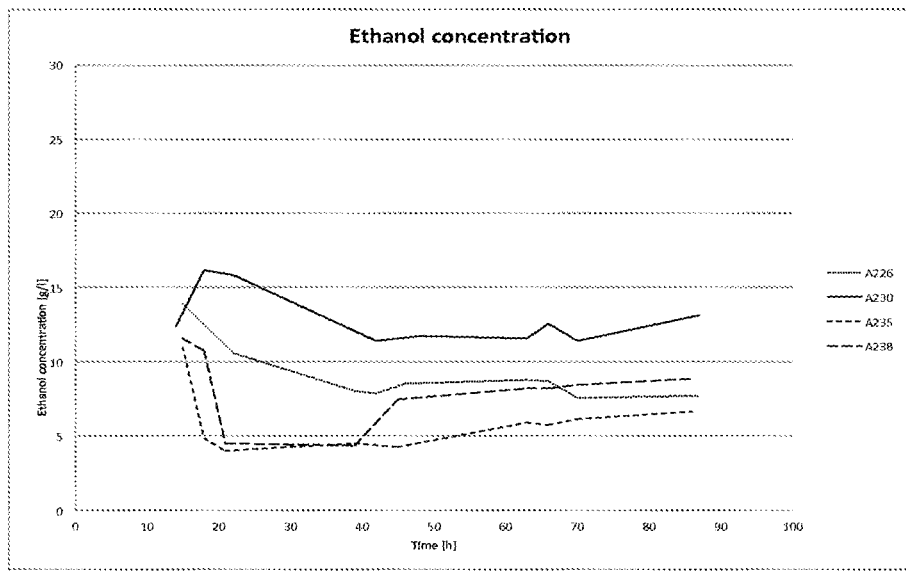
Figure 29: Ethanol concentration profile for 4 different feed rates indicating effect of RQ for mAb3 antibody Strain B in 20L fermentors
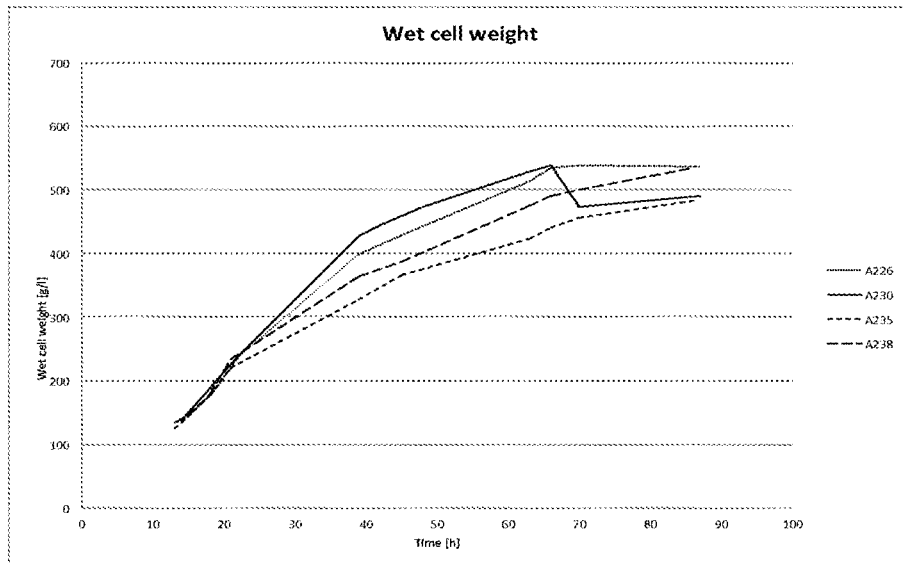
Figure 30: Cell growth profile for 4 different feed rates indicating cellular growth for mAb3 antibody Strain B in 20L fermentors

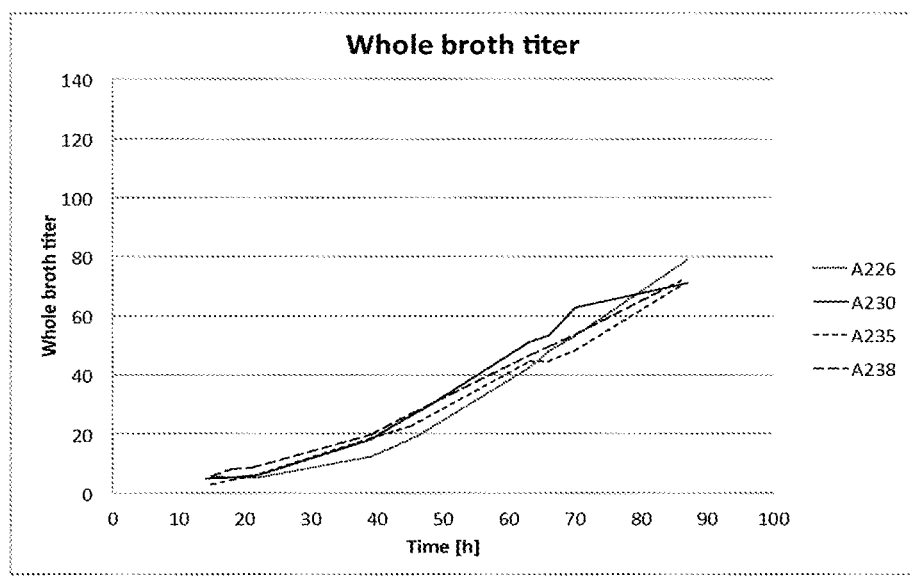
Figure 31: Whole Broth Titer profile for 4 different feed rates indicating product expression for mAb3 antibody Strain B in 20L fermentors mAb4

2 Feed Rates

A197 = mAb4 Strain A Feed rate = 13 g/l/hr, RQ = 1.09 – 1.15, No Etoh bolus
A198 = mAb4 Strain A Feed rate = 11 g/l/hr, RQ = 1.09 – 1.15, No Etoh bolus

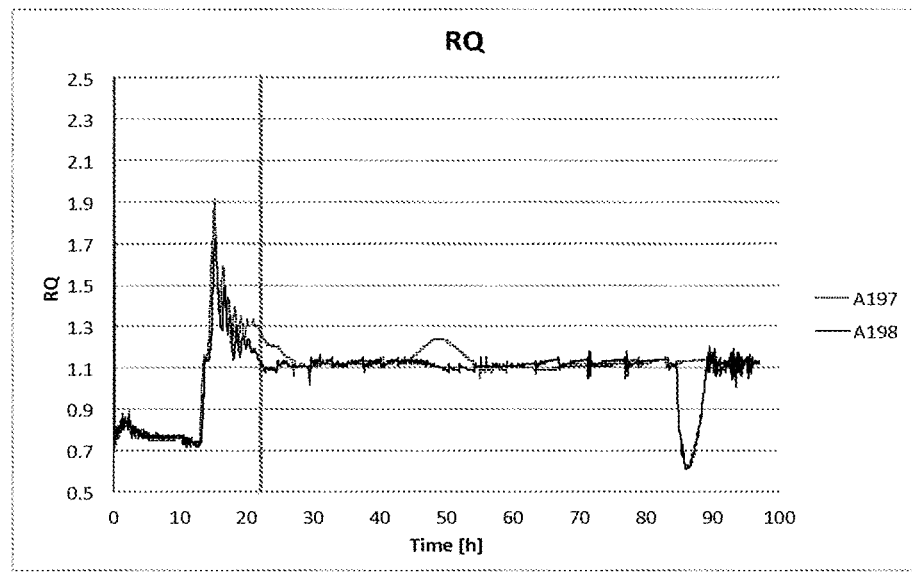

Figure 32: RQ control profile at different feed rates for mAb4 antibody Strain A with a different sequence in the CDR region in 20L fermentors

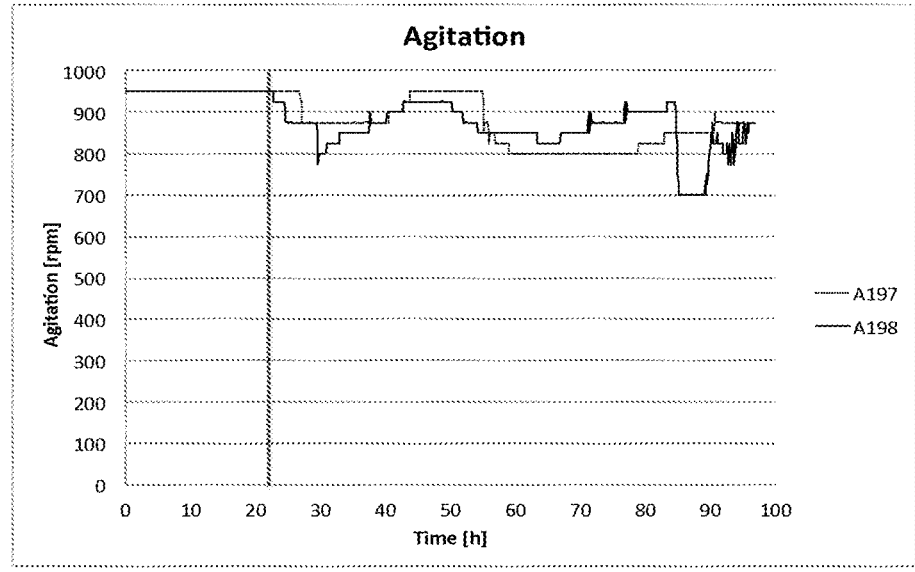

Figure 33: Agitation profile indicating agitation response to maintain desired RQ at different feed rates for mAb4 antibody Strain A with a different sequence in the CDR region in 20L fermentors

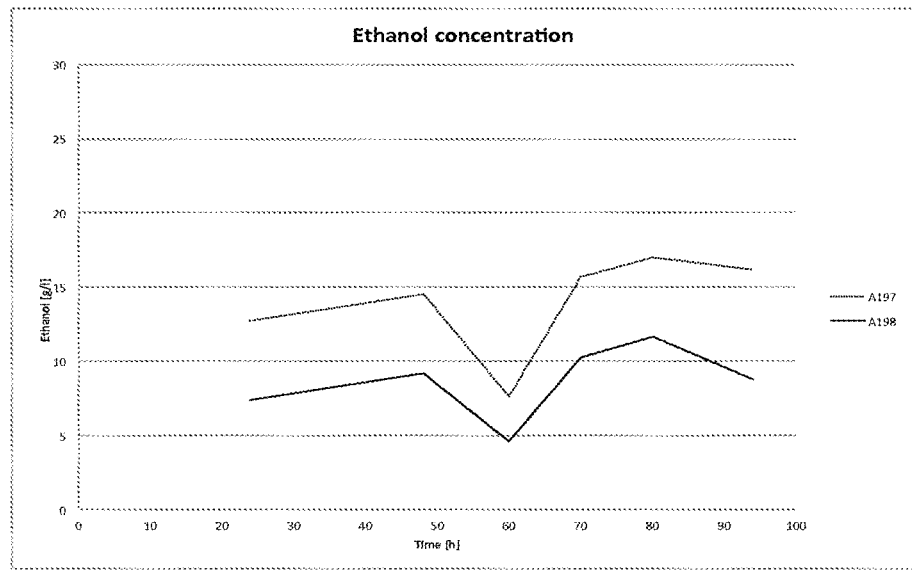
Figure 34: Ethanol concentration profile indicating effect of different feed rates for mAb4 antibody Strain A with a different sequence in the CDR region in 20L fermenters
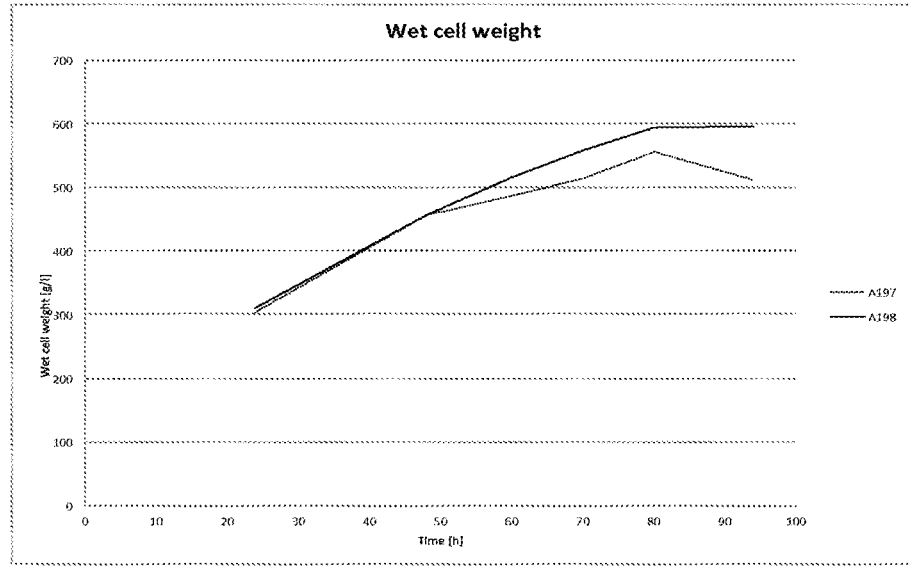
Figure 35: Cell growth profile indicating cellular growth at different feed rates for mAb4 antibody Strain A with a different sequence in the CDR region in 20L fermentors

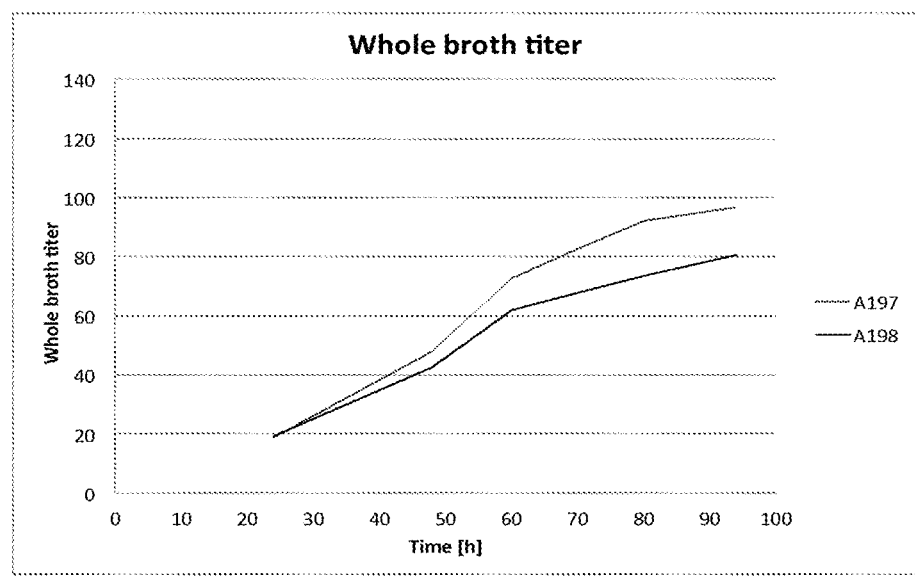
Figure 36: Whole Broth Titer profile indicating product expression at different feed rates for mAb4 antibody Strain A with a different sequence in the CDR region in 20L fermentors

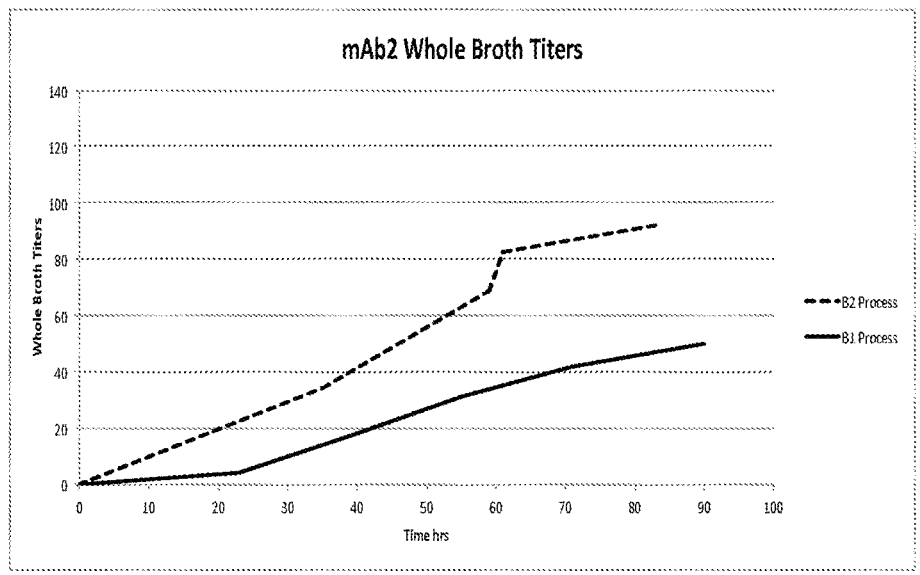
Figure 37: Whole Broth Titer profile indicating product expression for aerobic fermentation for mAb2 antibody Strain A in large scale fermentors

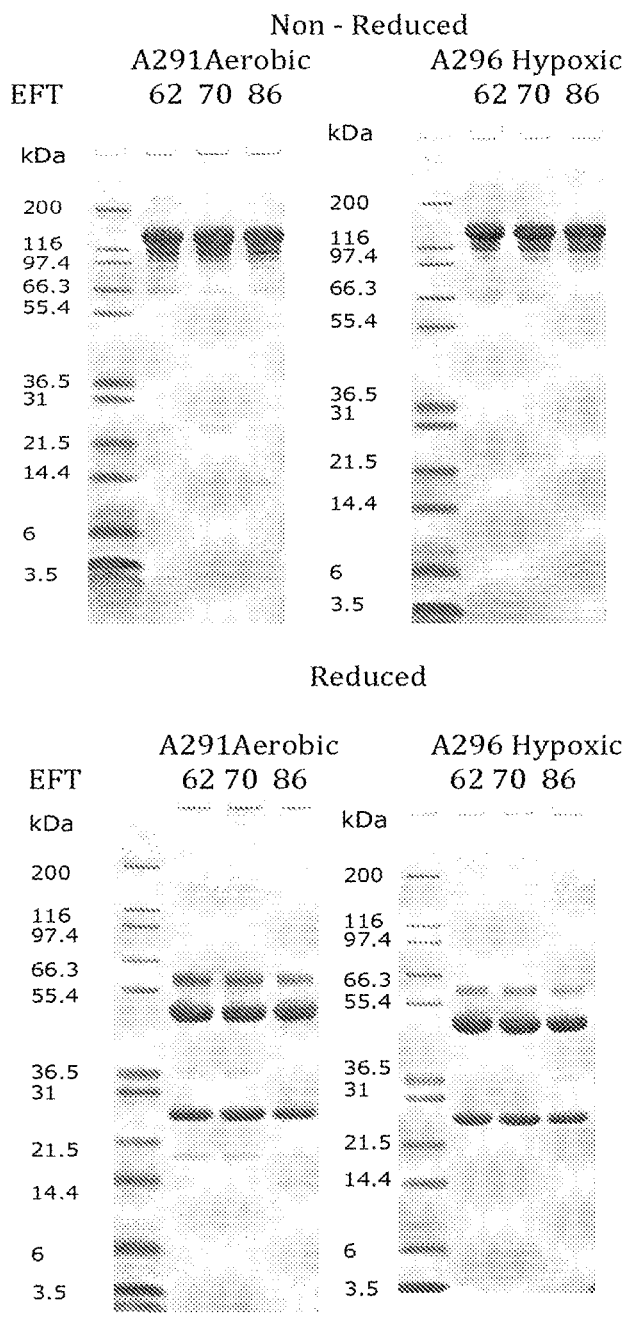
Figure 38: shows SDS – PAGE Non-reduced and reduced gel for aerobic fermentation and a hypoxic fermentation for mAb1 antibody Strain A at 3 different fermentation times in 20L fermentors

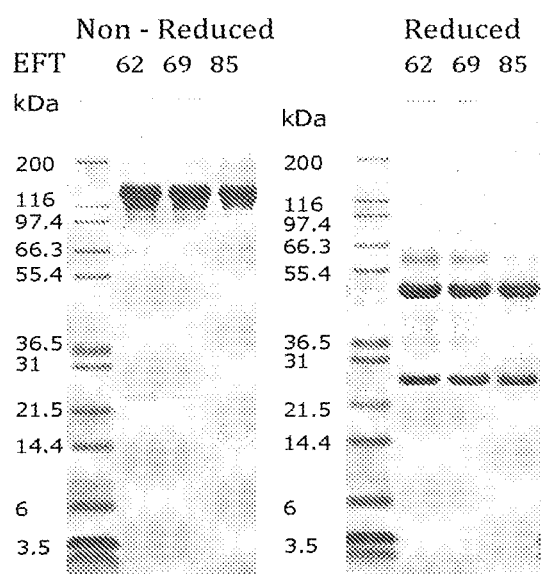
Figure 39: shows SDS-PAGE Non-reduced and reduced gel for hypoxic fermentation for mAb1 Strain A at 3 different fermentation times in 20L fermentors

FERMENTATION PROCESS FOR ANTIBODY PRODUCTION

RELATED APPLICATIONS

This application is a divisional of U.S. application Ser. No. 14/776,865 filed Sep. 15, 2015, which is a U.S. National Phase Application submitted under 35 U.S.C. 371 based on International Application No. PCT/US14/30311 filed Mar. 17, 2014 (published as WO 2014-145521 on Sep. 18, 2014), which claims priority to and benefit of U.S. Provisional Application No. 61/790,613 filed Mar. 15, 2013, each and all of which are hereby incorporated by reference in their entirety.

TECHNICAL FIELD OF THE INVENTION

This invention is related to the area of fermentation. In particular, it relates to fermentation of recombinant yeast cells.

BACKGROUND OF THE INVENTION

The yeast *Pichia pastoris* has previously is a suitable production host for the manufacture of recombinant proteins of therapeutic utility. Examples include the production of Human Serum Albumin and the Kallikrein inhibitor, Ecallantide (Reichert, J. mAbs 4:3 1-3, 2012). *Pichia pastoris* has been used for the production of recombinant monoclonal antibodies having correctly assembled heavy and light chains (U.S. Pat. No. 7,927,863). The glyceraldehyde-3-phosphate dehydrogenase (GAP) promoter can drive expression in yeast of an antibody lacking N-glycosylation in yeast (U.S. Pat. No. 7,927,863). Recent work by Baumann et. al. (*BMC Genomics* 2011, 12:218), using the GAP system to produce recombinant antibody Fab fragment has shown that this system, previously thought to be constitutive, exhibits increased expression under hypoxic conditions using glucose as the source of carbon and energy. Hypoxic conditions are those that allow the dissolved oxygen level in a fermentation to drop to very low levels while still supplying oxygen to the culture through aeration and agitation. This results in mixed aerobic and fermentative metabolism.

The use of hypoxic conditions in a fermentor can result in the toxic accumulation of ethanol, and care must be exercised to control the process such that toxic levels do not accumulate. Baumann accomplished this by measuring the level of ethanol in the fermentor and adjusting the glucose feed rate to reduce its accumulation. However this method is not very scalable, as technology for reliably measuring ethanol in large scale fermentors is not widely available.

There is a continuing need in the art for efficient and accurate production of recombinant proteins, especially antibody molecules, antibody fragments, and antibody constructs.

SUMMARY OF THE INVENTION

According to one embodiment of the invention a method is provided that produces a recombinant protein such as an antibody or antigen-binding fragment of an antibody in yeast cells. A population of yeast cells is cultured under fed-batch fermentation conditions in a culture medium. Each yeast cell comprises a DNA segment encoding a recombinant protein, such as a heavy chain polypeptide, and optionally a DNA segment encoding a second recombinant protein, such as a light chain polypeptide of an antibody. The one or more DNA segments are operably linked to a glyceraldehyde-3-phosphate (GAP) transcription promoter and a transcription terminator. The fermentation comprises a fermentable sugar feed at a first feed rate, and the fermentation is oxygenated at a first oxygen transfer rate. The respiratory quotient (RQ) of the population is measured during the feeding phase of the fed-batch fermentation and it is compared to a desired predetermined range. One or both of the fermentable sugar feed rate and the oxygen transfer rate are adjusted to a second rate when the RQ is outside of a desired predetermined range. The measuring and adjusting are performed throughout all or part of the culturing. The yeast cells are harvested from the culture medium. Recombinant proteins, such as heavy chain and light chain polypeptides produced by the yeast cells, are recovered from yeast cell-depleted culture medium or from the yeast cells.

According to another embodiment of the invention a method is provided for producing an antibody comprising two heavy chains and two light chains in *Pichia* yeast cells. A population of *Pichia* yeast cells is cultured under hypoxic, fed-batch fermentation conditions in a culture medium. Each yeast cell comprises a DNA segment encoding a heavy chain polypeptide and a DNA segment encoding a light chain polypeptide of an antibody. DNA segments are operably linked to a glyceraldehyde-3-phosphate (GAP) transcription promoter and a transcription terminator. The yeast cells are harvested from the culture medium. The antibody produced by the yeast cells is recovered from the yeast cells or from the yeast cell-depleted culture medium.

These and other embodiments which will be apparent to those of skill in the art upon reading the specification, provide the art with methods and products with improved reliability, predictability, efficiency, and quality.

BRIEF DESCRIPTION OF THE DRAWINGS

FIG. 1: shows the RQ profiles of 3 different Mab1 Strains A, B, and C. The vertical line indicates the time at which RQ control was initiated.

FIG. 2: shows the Agitation profiles of 3 different Mab1 Strains A, B, and C. The vertical line indicates the time at which RQ control was initiated.

FIG. 3: shows the Ethanol profiles of 3 different Mab1 Strains A, B, and C.

FIG. 4: shows the Growth profiles of 3 different Mab1 Strains A, B, and C.

FIG. 5: shows the Whole Broth Titer profiles of 3 different Mab1 Strains A, B, and C.

FIG. 6: shows the RQ profiles of Mab1 Strain A at 3 different RQ Set points RQ 1.09-1.15, 1.19-1.25, 1.29-1.35. The vertical line indicates the time at which RQ control was initiated.

FIG. 7: shows the Agitation profiles of Mab1 Strain A at 3 different RQ Set points RQ 1.09-1.15, 1.19-1.25, 1.29-1.35. The vertical line indicates the time at which RQ control was initiated.

FIG. 8: shows the Ethanol profiles of Mab1 Strain A at 3 different RQ Set points RQ 1.09-1.15, 1.19-1.25, 1.29-1.35

FIG. 9: shows the Growth profiles of Mab1 Strain A at 3 different RQ Set points RQ 1.09-1.15, 1.19-1.25, 1.29-1.35

FIG. 10: shows the Whole Broth Titer profiles of Mab1 Strain A at 3 different RQ Set points RQ 1.09-1.15, 1.19-1.25, 1.29-1.35

FIG. 11: shows the RQ profiles of Mab1 Strain A grown under aerobic and hypoxic conditions. The vertical line indicates the time at which RQ control was initiated.

FIG. 12: shows the Agitation profiles of Mab1 Strain A grown under aerobic and hypoxic conditions. The vertical line indicates the time at which RQ control was initiated.

FIG. 13: shows the Ethanol profiles of Mab1 Strain A grown under aerobic and hypoxic conditions FIG. 14: shows the Growth profiles of Mab1 Strain A grown under aerobic and hypoxic conditions FIG. 15: shows the % DO profiles of Mab1 Strain A grown under aerobic and hypoxic conditions FIG. 16: shows the Whole Broth Titer profiles of Mab1 Strain A grown under aerobic and hypoxic conditions FIG. 17: shows the RQ profiles of 4 different Mab2 Strains A, B, C and D. The vertical line indicates the time at which RQ control was initiated.

FIG. 18: shows the Agitation profiles of 4 different Mab2 Strains A, B, C and D strains. The vertical line indicates the time at which RQ control was initiated.

FIG. 19: shows the Ethanol profiles of 4 different Mab2 Strains A, B, C and D strains.

FIG. 20: shows the Growth profiles of 4 different Mab2 Strains A, B, C and D strains.

FIG. 21: shows the Whole Broth Titer profiles of 4 different Strains A, B, C and D strains.

FIG. 22: shows the RQ profiles of 3 different Mab3 Strains A, B, and C. The vertical line indicates the time at which RQ control was initiated.

FIG. 23: shows the Agitation profiles of 3 different Mab3 Strains A, B, and C. The vertical line indicates the time at which RQ control was initiated.

FIG. 24: shows the Ethanol profiles of 3 different Mab3 Strains A, B, and C.

FIG. 25: shows the Growth profiles of 3 different Mab3 Strains A, B, and C.

FIG. 26: shows the Whole Broth Titer profiles of 3 different Mab3 Strains A, B, and C.

FIG. 27: shows the RQ profiles of Mab3 Strain B at different feed rates. The vertical line indicates the time at which RQ control was initiated.

FIG. 28: shows the Agitation profiles of Mab3 Strain B at different feed rates. The vertical line indicates the time at which RQ control was initiated.

FIG. 29: shows the Ethanol profiles of Mab3 Strain B at different feed rates.

FIG. 30: shows the Growth profiles of Mab3 Strain B at different feed rates.

FIG. 31: shows the Whole Broth Titer profiles of Mab3 Strain B at different feed rates.

FIG. 32: shows the RQ profiles of Mab4 Strain A at different feed rates. The vertical line indicates the time at which RQ control was initiated.

FIG. 33: shows the Agitation profiles of Mab4 Strain A at different feed rates. The vertical line indicates the time at which RQ control was initiated.

FIG. 34: shows the Ethanol profiles of Mab4 Strain A strain at different feed rates.

FIG. 35: shows the Growth profiles of Mab4 Strain A strain at different feed rates.

FIG. 36: shows the Whole Broth profiles of Mab4 Strain A strain at different feed rates.

FIG. 37: shows the Whole Broth profiles of Mab2 Strain A for the aerobic (B1) and hypoxic (B2) process in large scale fermentation FIG. 38: shows the SDS-PAGE Non-Reduced and Reduced gels of Mab1 Strain A at fermentation times 62, 70, and 86 hours for aerobic and hypoxic process conditions FIG. 39: shows the SDS-PAGE Non-Reduced and Reduced gels of Mab1 Strain A at fermentation times 62, 69, and 85 hours

DETAILED DESCRIPTION OF THE INVENTION

The inventors have developed a process for making recombinant proteins in yeast which may employ a particular type of feedback control mechanism to increase the productivity of fermentations. That feedback control mechanism allows the robust and precise control of mixed aerobic and fermentative metabolism that stimulates optimal production of the desired product. This can be used to good effect to produce recombinant monoclonal proteins such as antibodies in yeast, particularly in *Pichia pastoris*, and more particularly using the glyceraldehyde-3-phosphate (GAP) promoter.

The process using the feedback control mechanism is applicable to the production of full-length, correctly assembled recombinant monoclonal antibodies, as well as to antibody fragments and other recombinant proteins, i.e., not glyceraldehyde-3-phosphate. The control mechanism that we employ is easy to mechanize and render automatic, thus eliminating much labor in monitoring and adjusting fermentation conditions. The process is applicable to production of a variety of antibodies and other recombinant proteins and is readily scalable to accommodate commercial, e.g., large scale, production needs.

The production process may use Respiratory Quotient (RQ) as a feedback control variable. RQ can be used to balance mass transfer parameters and/or fermentable sugar feed rate in order to maintain a hypoxic state in the culture while preventing the toxic accumulation of ethanol, a by-product of fermentative metabolism. RQ is defined as the molar rate of carbon dioxide produced divided by the molar rate of oxygen consumed in the culture. It can be measured by analyzing the exhaust gas coming from the fermentor for content of carbon dioxide and oxygen. This metabolic parameter can be measured continuously or intermittently throughout the desired growth phase using readily available means. Examples of appropriate intervals for measurements are hourly, half-hourly, quarter-hourly, ten minutes, five minutes, four minutes, three minutes, two minutes, one minute. Time periods during measurements may vary with growth conditions, from initiating the culture through harvest. Exemplary periods for measurement and control are between 20 and 40 hours, between 10 and 60 hours, between 5 and 70 hours, and between 20 and 110 hours after initiating of the culturing in the fermentor.

When yeast cells are grown in a completely anaerobic state, without the presence of oxygen, they are said to be using fermentative metabolism to produce the energy they need to grow. In this case the following stoichiometric equation for the conversion of glucose to ethanol applies:

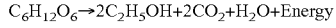

$C_6H_{12}O_6 \rightarrow 2C_2H_5OH + 2CO_2 + H_2O + \text{Energy}$

When yeast cells obtain their energy solely from aerobic metabolism of glucose, then oxygen is consumed, and only carbon dioxide and water are produced:

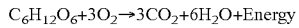

$C_6H_{12}O_6 + 3O_2 \rightarrow 3CO_2 + 6H_2O + \text{Energy}$

In the presence of oxygen, yeast cells use aerobic metabolism, which is more efficient, i.e., more energy is obtained from a mole of glucose under aerobic metabolism than under fermentative metabolism.

The RQ of a culture producing only ethanol from glucose approaches infinity (since no oxygen is consumed, the denominator of RQ is zero), whereas for purely aerobic metabolism of glucose the RQ approaches the value of 1.0 (three moles of oxygen are consumed to produce 3 moles of carbon dioxide). Thus values higher than 1 indicate a mixed metabolic condition where both aerobic and fermentative metabolism arc taking place simultaneously. Typically oxygen transfer rate and/or fermentable sugar feed rate can be adjusted using RQ as a feedback control variable to accomplish this mixed metabolism. Using such a mixed metabolism, hypoxic conditions can be maintained. A hypoxic state exists when there is a low level of fermentative metabolism controlled by the equilibrium of oxygen transfer rate and fermentable sugar feed rate. Hypoxic conditions may be defined by an RQ above 1.0 with dissolved oxygen below about 5%.

RQ can be measured in the exhaust gas stream from a fermentor. Any known and suitable method for ascertaining the molar concentration of oxygen consumed and carbon dioxide generated can be used. Exemplary techniques which may be used are mass spectrometry, infrared spectroscopy, and paramagnetic analysis.

Hypoxic growth has a beneficial effect on the production of full length, properly assembled proteins, such as antibodies, in Pichia. We tried to reduce the dissolved oxygen concentration simply by reduction of the agitator speed during fermentation. However, it was not possible to obtain reliable control in this manner, because small differences in agitation rate or fermentable sugar feed rate would quickly result in the accumulation of toxic levels of ethanol.

A feedback control mechanism can also be used to measure and control ethanol levels through modulation of either fermentable sugar feed rate and/or oxygen transfer rate, e.g., by agitator speed. Controlling accumulation of ethanol should permit a more stable process. In order to monitor ethanol levels one can use a probe inserted into the fermentor. The probe can monitor ethanol levels in the fermentation broth continuously. However, it is not feasible to use such a probe in commercial manufacturing of molecules under Good Manufacturing Processes, because it does not have an output that can be sufficiently calibrated.

When RQ is maintained in a narrow range from approximately 1.1 to approximately 2, ethanol accumulation stabilizes at levels that are not toxic. Preferably the concentration of ethanol is maintained between about 5 g/l and 17 g/l. Moreover, these same conditions stimulate the GAP promoter, leading to significantly increased recombinant protein, e.g., antibody production over aerobic fermentation conditions. RQ ranges that may be desirable include about 1.08-2.0; about 1.08-1.85; about 1.08-1.65; about 1.08-1.45; about 1.08-1.35; about 1.08-1.25; about 1.08-1.2; and about 1.08-1.15. Alternative carbon sources other than glucose can achieve an RQ less than 1. Such carbon sources include acetate and glycerol. Other suitable RQ ranges include 1.08 to 1.35, and 1.15 to 1.25. RQ can be monitored and controlled during any desired portion of the fermentation, for example from 0 to 110 hours, from 20-40 hours, from 20-70 hours, from 20-90 hours, from 20-110 hours, or any other desired time period.

Thus RQ can be manipulated and changed over time by addition of various carbon sources, by addition of various amounts of a carbon source, and by manipulation of the oxygen levels. In one embodiment, oxygen levels are manipulated by increasing or decreasing agitation. In another embodiment, the ratio of oxygen to nitrogen gas in the gas feed is controlled. Ways that the oxygen transfer rate can be adjusted include the changing the air flow rate, the oxygen concentration, the cell density, the temperature, and agitation. In another embodiment glucose or other fermentable sugar feed is modulated to affect the RQ. Other fermentable sugars which can be used in the feed include without limitation fructose, sucrose, maltose, and maltotriose. Feed rate or composition can be modulated to affect the RQ. The control of RQ may be manual or automatic.

Protein-encoding nucleic acids, e.g., encoding antibodies, may be on a single or multiple continuous or discontinuous segments of a recombinant construct. Antibodies may be any type of fragment or construct or full length. These may be, for example, Fab, F(ab')$_2$, Fc, and ScFv. In some embodiments, the chains and or chain fragments will assemble properly in vivo. If assembly is not proper, in vitro assembly may be necessary. Other proteins which may be desirably made are those having one or more subunits, whether heteromeric or homomeric. Typically the protein will be useful for diagnostic or therapeutic purposes. The protein may be a growth factor, a cytokine, a blood coagulation factor, a therapeutic toxin, a structural protein useful for reconstruction, an enzyme, etc.

Proteins such as antibodies may be recovered from the cell-depleted culture medium or from the cells by any technique known in the art. Typically a binding step will be used to reduce the volume of the preparation. Binding can be done on filters or columns or other solid supports, as is convenient. In some embodiments, protein A may be used as an antibody capturing agent. The protein A may be bound to a polymeric matrix.

Any type of yeast cells can be used, including *Saccharomyces*, *Hansenula*, and *Pichia* species. Exemplary but not limiting species which may be used are *P. pastoris*, *P. methanolica*, *P. angusta*, *P. thermomethanolica*, *Hansenula polymorpha*, and *S. cerevisiae*. The yeast may be haploid or diploid.

Other promoters like GAP may be used similarly. These are typically promoters that are for genes that are up-regulated in hypoxic, glucose-limiting growth in yeast cells, such as *Pichia*. Such promoters which may be used include, without limitation, promoters for genes YHR140W, YNL040W, NTA1, SGT1, URK1, PGI1, YHR112C, CPS1, PET18, TPA1, PFK1, SCS7, YIL166C, PFK2, HSP12, ERO1, ERG11, ENO1, SSP120, BNA1, DUG3, CYS4, YEL047C, CDC19, BNA2, TDH3, ERG28, TSA1, LCB5, PLB3, MUP3, ERV14, PDX3, NCP1, TPO4, CUS1, COX15, YBR096W, DOG1, YDL124W, YMR244W, YNL134C, YEL023C, PIC2, GLK1, ALD5, YPR098C, ERG1, HEM13, YNL200C, DBP3, HAC1, UGA2, PGK1, YBR056W, GEF1, MTD1, PDR16, HXT6, AQR1, YPL225W, CYS3, GPM1, THI11, UBA4, EXG1, DGK1, HEM14, SCO1, MAK3, ZRT1, YPL260W, RSB1, AIM19, YET3, YCR061W, EHT1, BAT1, YLR126C, MAE1, PGC1, YHL008C, NCE103, MIH1, ROD1, FBA1, SSA4, PIL1, PDC1-3, THI3, SAM2, EFT2, and INO1.

Large scale fermentation processes are those typically used in commercial processes to produce a useful product. Typically these are greater than 100 liters in volume. Fed-batch fermentation is a process by which nutrients are added during the fermentation to affect cell density and product accumulation.

Disclosures of prior published patent applications and patents, U.S. Pat. Nos. 7,927,863, 8,268,582, U.S. App 2012/0277408 are expressly incorporated herein.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLES

We show the applicability of the method to the production of four different humanized monoclonal antibodies. Each antibody is produced in *Pichia pastoris* using the glyceraldehyde-3-phosphate (GAP) promoter system.

Example 1

We found a difference in titers between aerobic and hypoxic cultures of antibody Mab2. Restricting the oxygen availability to the culture by reducing the agitation rate in the fermentor resulted in a significant increase in product formation. This was our first confirmation that hypoxic conditions, when applied to the production of full length antibodies, results in a significant increase in product formation for fully assembled, appropriately disulfide bonded humanized monoclonal antibodies. See FIG. 37.

Example 2

Three different strains of antibody Mab1, each with differing copy numbers, are grown in 20 liter fermentors using RQ control strategy (modulaton of agitation using feedback control that modulates agitator speed to maintain RQ at the desired level (in this case a value of 1.12) to promote mixed metabolism of hypoxic conditions in a controlled manner so as to ensure that ethanol concentrations do not reach toxic levels. In each case, the robust nature of the feedback control mechanism allows mixed metabolism without accumulation of toxic levels of ethanol (typically greater than 20 g/L). (See FIGS. 1-5)

Example 3

Mab1 is cultured under hypoxic condition using the RQ control strategy, at three different control set-points for RQ. In this case, increasing the RQ set-point increases the level of ethanol accumulation, reduces the accumulation of cells, but does not have a significant impact on the overall product accumulation. This shows the utility of the RQ method at set-points ranging from 1.09 to 1.35. (See FIGS. 6-10)

Example 4

We compared, for Mab1, the effect of hypoxic growth, as attained by RQ control, against the same process under aerobic conditions. The aerobic process results in lower ethanol production (as expected), and markedly lower product formation. (See FIGS. 11-16).

Example 5

The RQ control strategy was implemented on fermentations of Mab2 that had production strains varying in the number of copies of each heavy and light chain. This study shows the robust nature of the RQ strategy in controlling the accumulation of ethanol while providing a hypoxic environment for mixed metabolism. (See FIGS. 17-21).

Example 6

The RQ control strategy was implemented on fermentations of Mab3, that had production strains varying in the number of copies of each heavy and light chain. This study shows the robust nature of the RQ strategy in controlling the accumulation of ethanol while providing a hypoxic environment for mixed metabolism. (See FIGS. 22-26)

Example 7

Strains of Mab3, containing varying copies of Heavy Chain and of Light Chain is grown using the RQ control strategy but incorporating varying glucose feed rates. Again, the RQ strategy allows for effective control of ethanol levels, resulting in very similar product accumulation rates. This provides further evidence of the robustness of the RQ strategy to a variety of fermentation conditions. (See FIGS. 27-31).

Example 8

The RQ strategy is demonstrated for MAb4, which binds to the same target as MAb1, but has a different sequence in its CDR than MAb1. We compared two different rates of glucose feed. Once again the strategy allowed for a stable ethanol concentration and similar antibody accumulation rates. (See FIGS. 32-36).

Example 9

The Fermentation Process for the Production of Antibodies or Antigen-Binding

Fermentation Media

Inoculum Medium is described below in Table 1.

TABLE 1

| Inoculum Medium | |
|---|---|
| Component[1] | Final concentration |
| Yeast extract | 30 g/l |
| $KH_2PO_4$ | 27.2 g/l |
| Glycerol or Glucose | 20 g/l |
| Yeast nitrogen base w/o amino acids | 13.4 g/l |
| Biotin | 0.4 mg/l |

[1]Keeping the same molarity, any chemical (X $nH_2O$; n ≥ 0) can be replaced by another chemical containing the same activated ingredient but various amount of water (X $kH_2O$; k ≠ n).

Seed Fermentation Medium

Medium is described below in Table 2.

| Composition Seed Fermentation Medium | |
|---|---|
| Component[1] | Final concentration |
| Sodium citrate dihydrate | 10.0 g/l |
| $MgSO_4$—$7H_2O$ | 3.7 g/l |
| $NH_4H_2PO_4$ | 36.4 g/l |
| $K_2HPO_4$ | 12.8 g/l |
| $K_2SO_4$ | 18.2 g/l |
| Glycerol, anhydrous | 40.0 g/l |
| Yeast extract | 30.0 g/l |
| Antifoam 204 | 0.5 ml/l |
| Trace mineral solution (PTM1) | 4.35 ml/l |

[1]Keeping the same molarity, any chemical (X $nH_2O$; n ≥ 0) can be replaced by another chemical containing the same activated ingredient but various amount of water (X $kH_2O$; k ≠ n).

Trace Mineral Solution is described below in Table 3.

TABLE 3

Trace Mineral Solution (PTM1)

| Component[1] | Final concentration |
|---|---|
| $ZnCl_2$[1] or Zinc Sulphate Heptahydrate[2] | 20 g/l[1] or 35 g/l[2] |
| $FeSO_4$—$7H_2O$ | 65 g/l |
| 95-98% $H_2SO_4$ | 5 ml/l |
| NaI | 0.08 g/l |
| $MnSO_4$—$2H_2O$ | 3 g/l |
| $Na_2MoO_4$—$2H_2O$ | 0.2 g/l |
| $H_3BO_3$ | 0.02 g/l |
| $CoCl_2$ | 0.5 g/l |
| $CuSO_4$—$5H_2O$ | 6 g/l |
| Biotin | 0.2 g/l |

[1]Keeping the same molarity, any chemical (X $nH_2O$; n ≥ 0) can be replaced by another chemical containing the same activated ingredient but various amount of water (X $kH_2O$; k ≠ n).

When all components are completely dissolved in DI water, filter sterilize through a sterile 0.2 μm filter.

Production Culture Batch Medium is described below in Table 4

TABLE 4

Production Culture Batch Medium

| Component1 | Final concentration |
|---|---|
| Sodium citrate dihydrate | 10.0 g/l |
| MgSO4—7H2O | 3.7 g/l |
| NH4H2PO4 | 35.6 g/l |
| K2HPO4 | 12.8 g/l |
| K2SO4 | 18.2 g/l |
| Glycerol, anhydrous | 40.0 g/l |
| Yeast extract | 30.0 g/l |
| Antifoam 204 | 1.6 ml/l |

1Keeping the same molarity, any chemical (X $nH2O$; n ≥ 0) can be replaced by another chemical containing the same activated ingredient but various amount of water (X $kH2O$; k ≠ n).

The above is sterilized by autoclaving at 121° C. for a minimum of 20 minutes. After sterilization and cooling, 4.35 ml/l of trace mineral solution (PTM1) is added to the Production Culture Batch Medium. Prior to inoculation of the fermentor, Production Culture Batch Medium containing 4.35 ml/l of PTM1 should be adjusted to pH 6.0 with 24-30% $NH_4OH$. The above values should be based on the total fermentation starting volume, including both medium and inoculum culture.

Glucose/Yeast Extract Feed Solution is described below in Table 5.

| Component[1] | Final concentration |
|---|---|
| Dextrose, anhydrous | 500 g/l |
| Yeast extract | 50 g/l |
| $MgSO_4$—$7H_2O$ | 3 g/l |
| Antifoam 204 | 0.1 ml/l |
| Sodium citrate dihydrate | 1.66 g/l |
| PTM1 | 12 ml/l |

[1]Keeping the same molarity, any chemical (X $nH_2O$; n ≥ 0) can be replaced by another chemical containing the same activated ingredient but various amount of water (X $kH_2O$; k ≠ n).

Ethanol bolus composition is described below in Table 6.

| Component[1] | Final concentration |
|---|---|
| Ethanol, 200 Proof | 11 g/l |

[1]Optionally a more dilute solution of ethanol can be used to achieve the same final concentration.

Fermentation Process

The fermentation process for the production of antibodies or antigen-binding fragments is accomplished by yeast, such as *P. pastoris*. The fermentation is initiated from the thawing of a frozen vial of a working cell bank. The thawed cells are then propagated in shake flasks. The culture from the shake flask is then used in the Inoculum Step, followed by a fed-batch process for the production of antibody. Optionally, the inoculum can be used to propagate cells in a seed batch fermentation, which can then be used to inoculate the production fermentor.

1. Inoculum Step

Thawed cells of the working cell bank are transferred to a baffled shake flask (1 to 4 baffles) that contains 8-20% of the working volume capacity of the flask Inoculum Medium. Thawed working cell bank is added at 0.1-1.0% of the volume of inoculum medium to the shake flask. The inoculum culture is incubated at 29-31° C. at an agitation speed of 220-260 rpm. The seed culture is harvested once reaching a cell density correlated to the absorbance at 600 nm ($OD_{600}$) of 15-30 (optimally 20-30). The culturing time is usually 20-26 hours (optimally 23-25 hours).

2. Seed Fermentation Batch Fermentation (Optional)

Fermentor is inoculated with inoculum from "Inoculum Step"

Inoculum=0.3% of seed fermentor medium volume

Temp: 30° C.

% DO: 30% pH: 6.0

Agitation: Cascade Strategy from 100-490 RPM

Airflow: 1 vvm ((volume of air/volume of starting fermentor media)/minute) Pressure: 0.2 bar Oxygen supplementation will occur when maximum agitation is reached with a corresponding decrease in airflow to maintain a constant vvm, to maintain the desired % DO set point of 30%

Continue Monitoring for DO Spike.

When a DO Spike has occurred which is indicated by a decrease in Agitation and an increase in DO, denoting that the carbon source (glycerol or glucose) has been completely utilized and the measured optical density, $OD_{600}$, is greater than 20, transfer a volume of the seed batch fermentation or inoculum culture which is equal to 1.0-10% of the Production fermentor Starting Batch Volume.

3. Batch Culture Phase

The batch culture is initiated by inoculation of the fermentor with the seed culture and ended with the depletion of glycerol. The fermentor contains prepared Production Culture Batch medium at 30-40% of maximum working volume. The seed culture is used to create a 1-10% inoculum within the fermentor. The initial engineering parameters are set as follows:

Temperature: 27-29° C.;

Agitation (P/V): 2-16 KW/$m^3$

Headspace Pressure: 0.7-0.9 Bar

Air flow: 0.9-1.4 VVM (volumes of air per volume of culture per minute, based on starting volume)

DO: no control pH: 5.9 to 6.1, controlled by 24-30% $NH_4OH$

The starting agitation speed and airflow are kept constant during the Batch Culture Phase in order to meet the initial power per volume (P/V) and volume per volume per minute (VVM) requirements. Batch Culture Phase is ended by starting feed when glycerol is depleted. The depletion of glycerol is indicated the dissolved oxygen (DO) value spike. The DO spike is defined as when the value of the DO increases by greater than 30% within a few minutes. Batch Culture Phase usually lasts 10-15 hours (optimally 11-13 hours).

4. Ethanol Bolus Addition (Optional)

Upon observation of the DO spike as mentioned above, 8-16 g/l of Ethanol, 200 Proof as a bolus is added into the fermentor. This usually occurs within 12-14 hours of Batch Culture Phase.

5. Fed-Batch Culture Phase

Feed to the fermentor with Glucose/Yeast Extract Feed Solution is initiated after the DO spike and after Ethanol Bolus Addition, around 12-14 hours within Batch Culture Phase and continues to the end of the fermentation. The rate of Glucose/Yeast Extract Feed Solution feed is set to allow for 6-11 g of glucose/l of starting volume per hour. The start of Glucose/Yeast Extract Feed Solution begins Fed-batch Culture Phase.

6. RQ Control Start

Respiratory Quotient (RQ) Control begins 8 hours after Fed-batch Culture Phase start. The initial RQ set points arc in the range of 1.09 to 1.35. Agitation is used to control the RQ. Agitation is cascaded off of the RQ control set point. RQ control starts at approximately 20-22 hours from the onset of Batch Culture Phase and continues to the end of the fermentation. The duration of RQ control lasts approximately 60 to 90 hours.

The agitation is adjusted in order to maintain a set level of RQ. The RQ Control strategy is detailed as follows:

RQ Hi Control set point: 1.35
RQ Low Control set point: 1.08
Maximum agitator set point: 255-950 rpm
Minimum agitator set point: 150-300 rpm
Agitator step change (change at each Wait Time interval): 3-25 rpm
Wait Time (time between evaluations): 3-10 minutes Ethanol/RQ Control Strategy This strategy has been incorporated to ensure that the ethanol concentration does not exceed a maximum value that can be toxic to the cells, and does not exceed a minimum value that could reduce product expression.

Example 10

FIG. 38 show SDS-PAGE gels of Mab1 produced under both hypoxic and aerobic conditions. For the non-reduced gel, in addition to the main band at 150 kD, additional bands below the main band indicate product heterogeneity with respect to the level of interchain disulfide bridging. These gels show that the level of heterogeneity is reduced by the use of hypoxic conditions. The increased homogeneity of the full length, completely cross-linked product indicates increased purity, i.e., increased desired product relative to other proteins present.

FIG. 38 also shows the reduced SDS-PAGE gel for the same samples. In this case expected bands at 25 kD and 50 kD represent the heavy and light chains of the antibody. The additional bands, particularly the one above the Heavy chain at approximately 55 kD represent the present of variant species of the antibody. These gels show a dramatic reduction in the presence of this variant when the cells are grown under hypoxic conditions, as compared with the aerobic culture.

We claim:

1. A method for producing a recombinant antibody polypeptide in *Pichia pastoris* yeast cells, wherein said antibody polypeptide is selected from the group comprising (i) a full-length antibody comprising two heavy chains and two light chains,
(ii) an antigen-binding fragment of an antibody comprising heavy chain fragments and light chain fragments, and
(iii) a single chain antigen-binding peptide,
wherein said chains and/or chain fragments assemble in vivo,
the method comprising the steps of:
a) culturing under fed-batch fermentation conditions a population of *Pichia pastoris* yeast cells in a culture medium,
   wherein said fed-batch fermentation conditions are effected after an inoculum expansion step, optionally a seed batch fermentation step, and a batch culture phase, which batch culture phase is initiated after said inoculum expansion and said optional seed batch fermentation steps,
   wherein each *Pichia pastoris* yeast cell comprises at least one DNA segment encoding said antibody polypeptide,
   wherein each of said at least one DNA segments operably linked to a glyceraldehyde-3-phosphate (GAP) transcription promoter and a transcription terminator,
   wherein the fed-batch fermentation comprises a fermentable sugar feed at a first feed rate, and
   wherein the fed-batch fermentation is agitated at a first oxygen transfer rate;
b) measuring respiratory quotient (RQ) of the population during the fed-batch fermentation and determining if it is within a desired predetermined range, wherein the desired predetermined range of RQ at about 20-40 hours after initiation of the batch culture phase consists of a range between 1.08 and 1.35, which corresponds to a mixed metabolic condition wherein both aerobic and fermentative metabolism are taking place simultaneously;
c) adjusting one or both of the fermentable sugar feed rate to a second feed rate or the oxygen transfer rate to a second oxygen transfer rate, when the RQ is outside of a desired predetermined range;
d) repeating steps (b) and (c) one or more times throughout the step of culturing;
e) harvesting the *Pichia pastoris* yeast cells from the culture medium; and
f) recovering the antibody polypeptide from the *Pichia pastoris* yeast cells and/or the culture medium, wherein the homogeneity of the fully assembled, completely cross-linked, that is disulfide-bonded, recovered antibody polypeptide is increased and/or the presence of aberrantly disulfide-bonded variants is decreased compared to an identical culture grown under aerobic conditions.

2. The method of claim 1 wherein step (d) is performed at intervals of between about 1 and 5 minutes, at intervals of about 3 minutes, or is performed continuously.

3. The method of claim 1 wherein step (c) is performed automatically using a feedback control mechanism linked to a device which measures the RQ.

4. The method of claim 1 further comprising the step of: delivering ethanol to the *Pichia pastoris* yeast cells at about 10 to 14 hours after initiation of the batch culture phase to achieve a level in the fermentation of about 8.0 to about 12.0 g/l ethanol.

5. The method of claim 1 comprising one or more of the following: (i) at least the desired predetermined range of RQ at about 20-40 hours after initiation of the batch culture phase is between 1.08 and 1.35, (ii) the step of harvesting is performed at about 80-110 hours after the initiation of the batch culture phase, (iii) ethanol concentration is measured during the step of fed-batch culturing, and adjustments are made to stabilize the ethanol concentration above about 5 g/l and below about 25 g/l, wherein said adjustments are made by adjusting one or both of the fermentable sugar feed rate to a third feed rate or the oxygen transfer rate to a third oxygen transfer rate, to stabilize the ethanol concentration above about 5 g/l and below about 17 g/l.

6. The method of claim 5 wherein the desired predetermined range of RQ at 20-110 hours after initiation of the batch culture phase of fermentation is selected from the group consisting of:
1.08-1.1;
1.08-1.15;
1.08-1.2;
1.08-1.25;
1.08-1.3; and
1.08-1.35.

7. The method of claim 1 wherein step (b) of measuring is performed by sampling the exhaust gas of the fermentation, or step (b) of measuring is performed using a mass spectrometer, infrared analyzer, or paramagnetic analyzer.

8. The method of claim 1 wherein in step (c) the oxygen transfer rate is adjusted, either by increasing the oxygen transfer rate when the RQ is too high or decreasing the oxygen transfer rate when the RQ is too low or the fermentable sugar feed rate is adjusted, either by increasing the fermentable sugar feed rate when the RQ is too low or decreasing the fermentable sugar feed rate when the RQ is too high or the fermentable sugar feed rate is also adjusted, either by increasing the fermentable sugar feed rate when the RQ is too low and decreasing the fermentable sugar feed rate when the RQ is too high or is performed by modulating agitation rate of the culture.

9. The method of claim 1 wherein the antibody polypeptide is harvested from the culture medium.

10. A method for producing an antibody comprising two heavy chains and two light chains in *Pichia* yeast cells, comprising the steps of:

culturing under hypoxic, fed-batch fermentation conditions a population of *Pichia* yeast cells in a culture medium, wherein said fed-batch fermentation conditions are effected after an inoculum expansion step, a seed batch fermentation step, and a batch culture phase, which batch culture phase is initiated after said inoculum expansion and said optional seed batch fermentation steps, wherein each yeast cell comprises a DNA segment encoding a heavy chain polypeptide and DNA segment encoding a light chain polypeptide of an antibody, wherein each of said DNA segments are operably linked to a glyceraldehyde-3-phosphate (GAP) transcription promoter and a transcription terminator, and wherein the RQ is maintained within desired predetermined range to represent a mixed metabolic condition wherein both aerobic and fermentative metabolism are taking place simultaneously;

harvesting the yeast cells from the culture medium; and recovering the antibody produced by the yeast cells from the yeast cell-depleted culture medium, wherein the homogeneity of the fully assembled, completely cross-linked, that is disulfide-bonded, recovered antibody polypeptide is increased and/or the presence of aberrantly disulfide-bonded variants is decreased compared to an identical culture grown under aerobic conditions, and further wherein the *Pichia* yeast cells are selected from the group consisting of *Pichia pastoris, Pichia methanolica, Pichia angusta*, and *Pichia thermomethanolica*.

* * * * *